(12) United States Patent
Arambula et al.

(10) Patent No.: US 7,166,113 B2
(45) Date of Patent: Jan. 23, 2007

(54) POLAR COORDINATE SURGICAL GUIDEFRAME

(75) Inventors: Jared Arambula, San Diego, CA (US); Kevin Foley, Germantown, TN (US); James F. Marino, La Jolla, CA (US); Alan Curtis Stone, San Diego, CA (US); Eric Finley, San Diego, CA (US); David Matsuura, Escondido, CA (US); Troy Woolley, San Diego, CA (US); Jamil Elbanna, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1101 days.

(21) Appl. No.: 09/888,223

(22) Filed: Jun. 22, 2001

(65) Prior Publication Data

US 2002/0007188 A1 Jan. 17, 2002

Related U.S. Application Data

(60) Provisional application No. 60/226,781, filed on Aug. 21, 2000, provisional application No. 60/213,730, filed on Jun. 22, 2000.

(51) Int. Cl.
*A61B 19/00* (2006.01)
(52) U.S. Cl. .................. 606/130; 600/417; 600/429
(58) Field of Classification Search ................. None
See application file for complete search history.

(56) References Cited

U.S. PATENT DOCUMENTS 2,666,430 A    1/1954 Gispert
3,115,140 A *  12/1963 Volkman ................ 607/116
3,941,127 A *  3/1976 Froning ................ 604/506
4,254,763 A    3/1981 McCready et al.
4,350,159 A    9/1982 Gouda
4,457,300 A    7/1984 Budde
4,592,352 A *  6/1986 Patil ..................... 606/130
4,638,798 A    1/1987 Shelden et al.
4,638,799 A    1/1987 Moore
4,653,509 A    3/1987 Oloff et al.
4,672,957 A    6/1987 Hourahane
4,706,665 A * 11/1987 Gouda ................... 606/130
4,722,336 A    2/1988 Kim et al.
4,723,544 A    2/1988 Moore et al.
4,750,487 A *  6/1988 Zanetti .................. 606/130
4,805,599 A    2/1989 Ray
4,841,967 A    6/1989 Chang et al.
4,926,849 A    5/1990 Downey
4,953,540 A    9/1990 Ray et al.
4,969,888 A   11/1990 Scholten et al.
5,078,140 A    1/1992 Kwoh
5,080,662 A *  1/1992 Paul .................... 606/130
5,108,404 A    4/1992 Scholten et al.

(Continued)

*Primary Examiner*—Glenn K. Dawson
(74) *Attorney, Agent, or Firm*—Jonathan D. Spangler

(57) ABSTRACT

A surgical instrument positioning system, comprising: at least one support; a cross member having at least one curved end portion, the at least one curved end portion being held by the at least one support such that the cross member is rotatable about an axis extending through a center of curvature of the at least one curved end portion of the cross member; and at least one surgical instrument holder suspended from the cross member.

A laser alignment system for an image intensifier, comprising: at least one laser source which emits planar laser beams in first and second intersecting planes.

56 Claims, 28 Drawing Sheets

U.S. PATENT DOCUMENTS

| | | |
|---|---|---|
| 5,147,372 A * | 9/1992 | Nymark et al. ............. 600/429 |
| 5,242,455 A * | 9/1993 | Skeens et al. .............. 606/130 |
| 5,269,305 A * | 12/1993 | Corol ......................... 600/429 |
| 5,280,427 A * | 1/1994 | Magnusson et al. ........ 600/407 |
| 5,284,130 A | 2/1994 | Ratliff |
| 5,308,352 A | 5/1994 | Koutrouvelis |
| 5,330,485 A * | 7/1994 | Clayman et al. ............ 606/130 |
| 5,397,323 A | 3/1995 | Taylor et al. |
| 5,528,651 A | 6/1996 | Leksell et al. |
| 5,575,798 A * | 11/1996 | Koutrouvelis ............... 606/130 |
| 5,598,269 A | 1/1997 | Kitaevich et al. |
| 5,618,288 A * | 4/1997 | Calvo ......................... 606/130 |
| 5,665,095 A | 9/1997 | Jacobson |
| 5,693,030 A | 12/1997 | Lee et al. |
| 5,746,735 A | 5/1998 | Furumoto et al. |
| 5,769,820 A | 6/1998 | Rammler |
| 5,805,661 A | 9/1998 | Leksell et al. |
| 5,853,366 A | 12/1998 | Dowlatshahi |
| 5,891,158 A * | 4/1999 | Manwaring et al. ........ 606/130 |
| 5,984,930 A * | 11/1999 | Maciunas et al. ........... 606/130 |
| 6,283,977 B1 * | 9/2001 | Ericsson et al. ............ 606/130 |
| 6,409,735 B1 * | 6/2002 | Andre et al. ................ 606/130 |
| 6,530,930 B1 * | 3/2003 | Marino et al. .............. 606/130 |

* cited by examiner

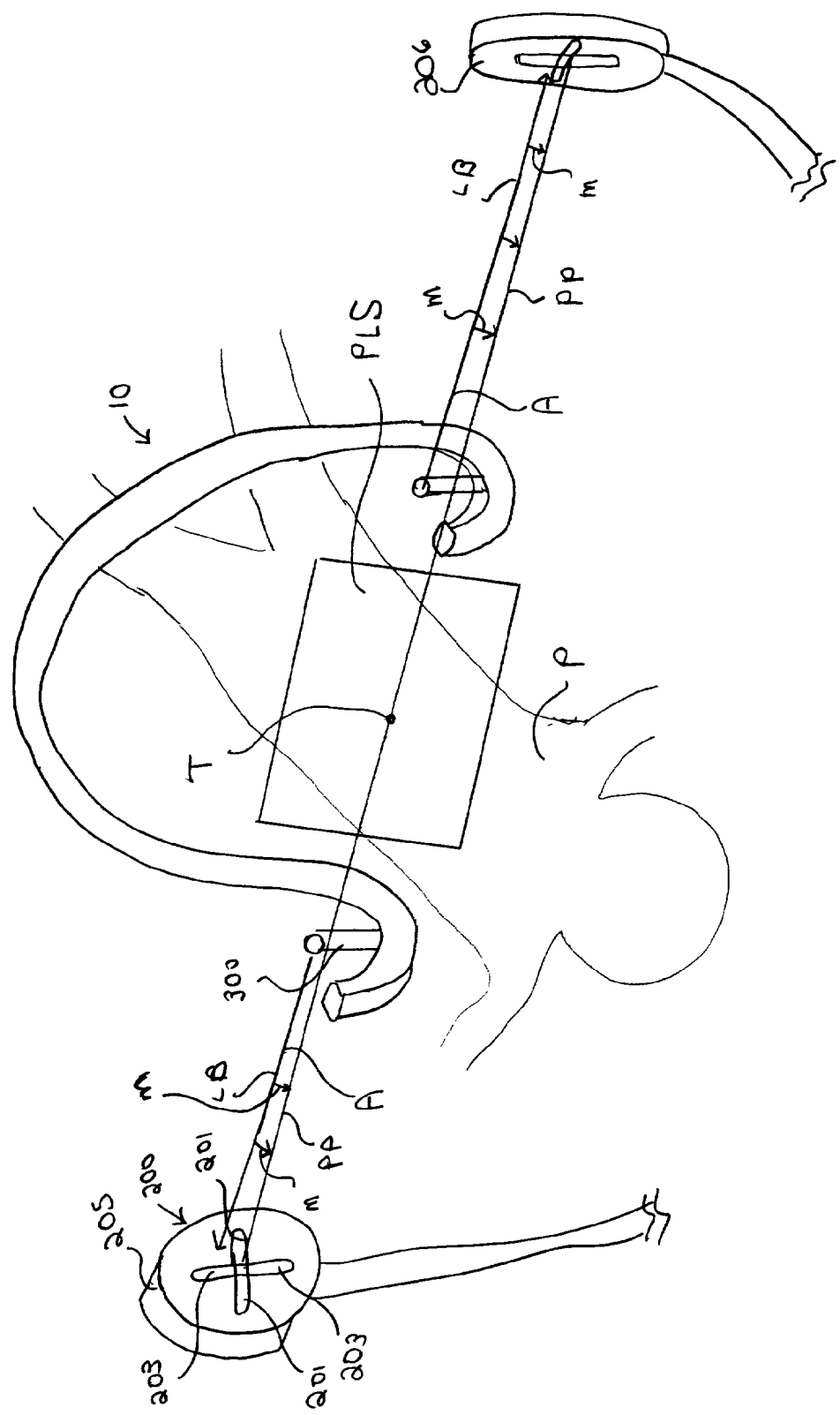

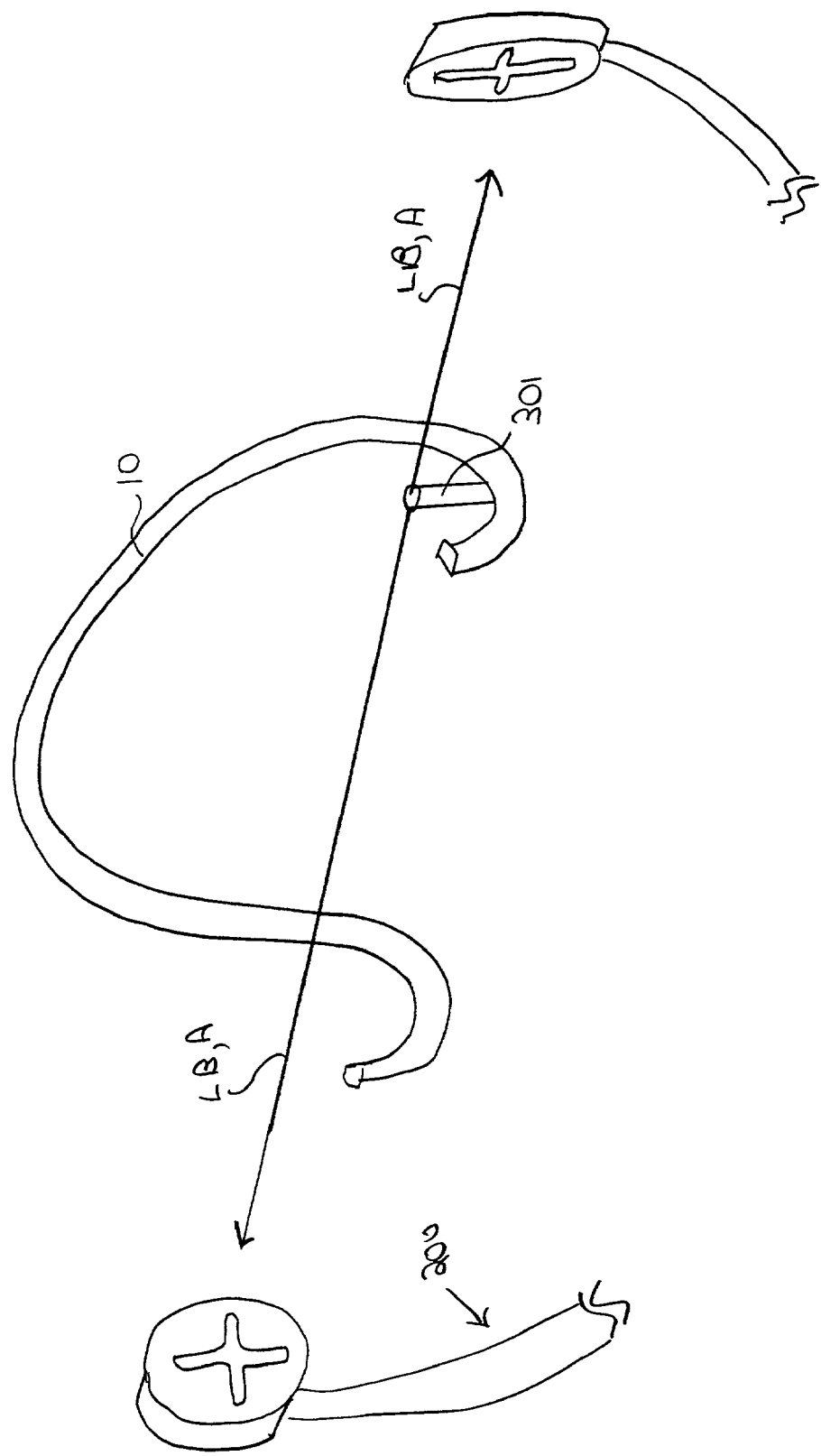

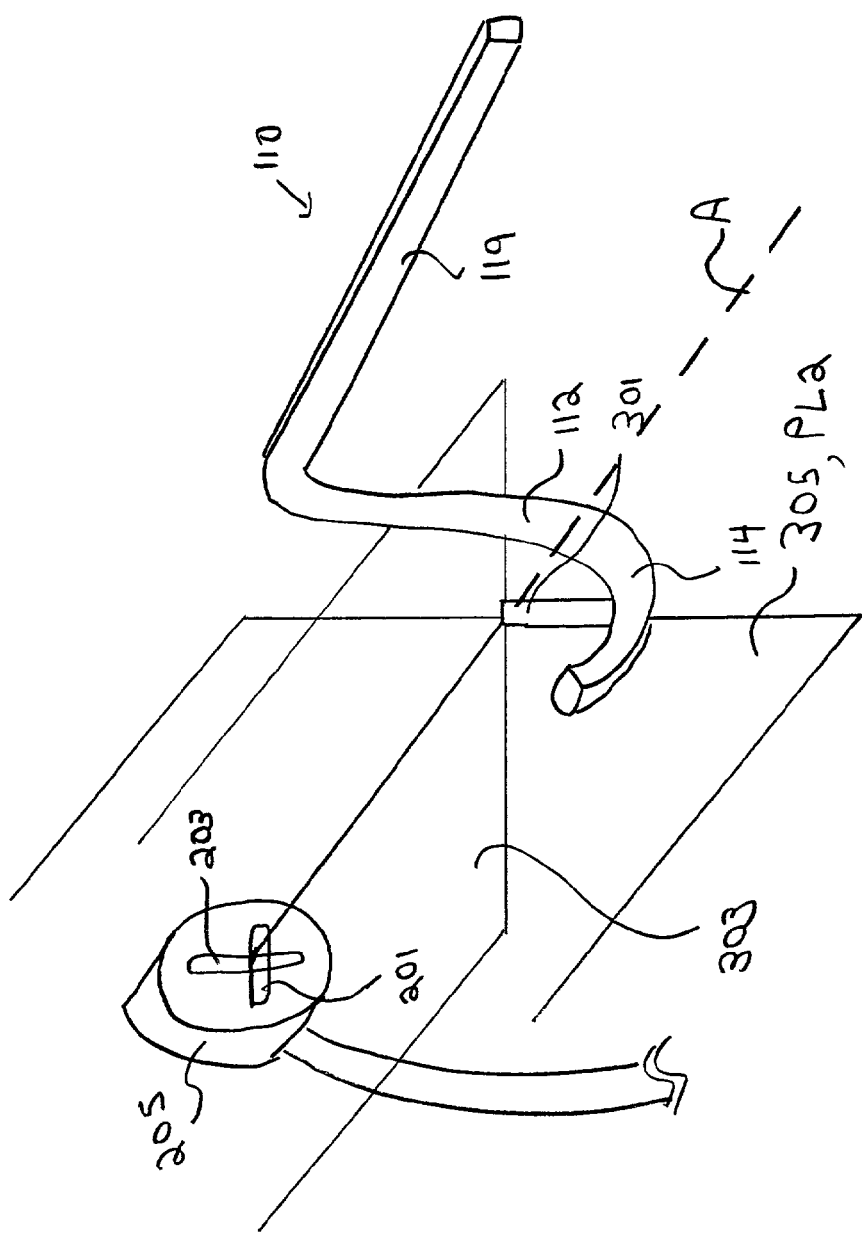

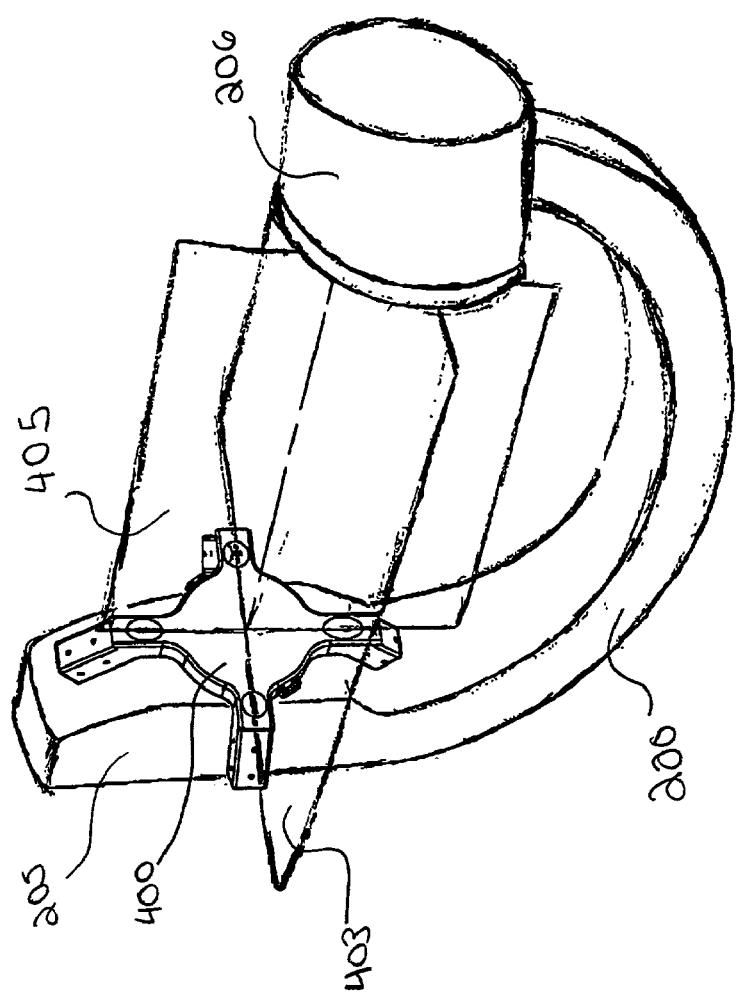

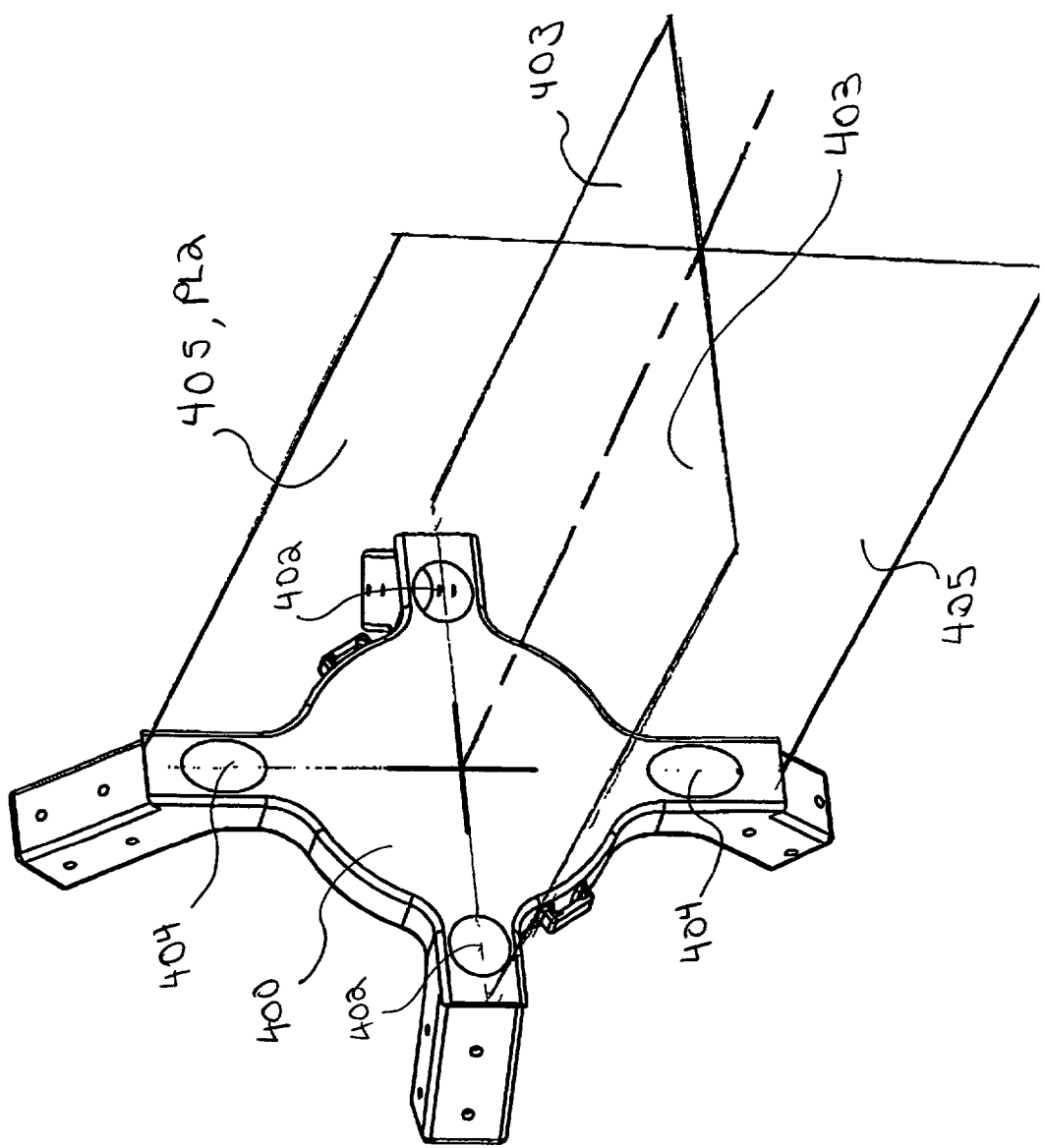

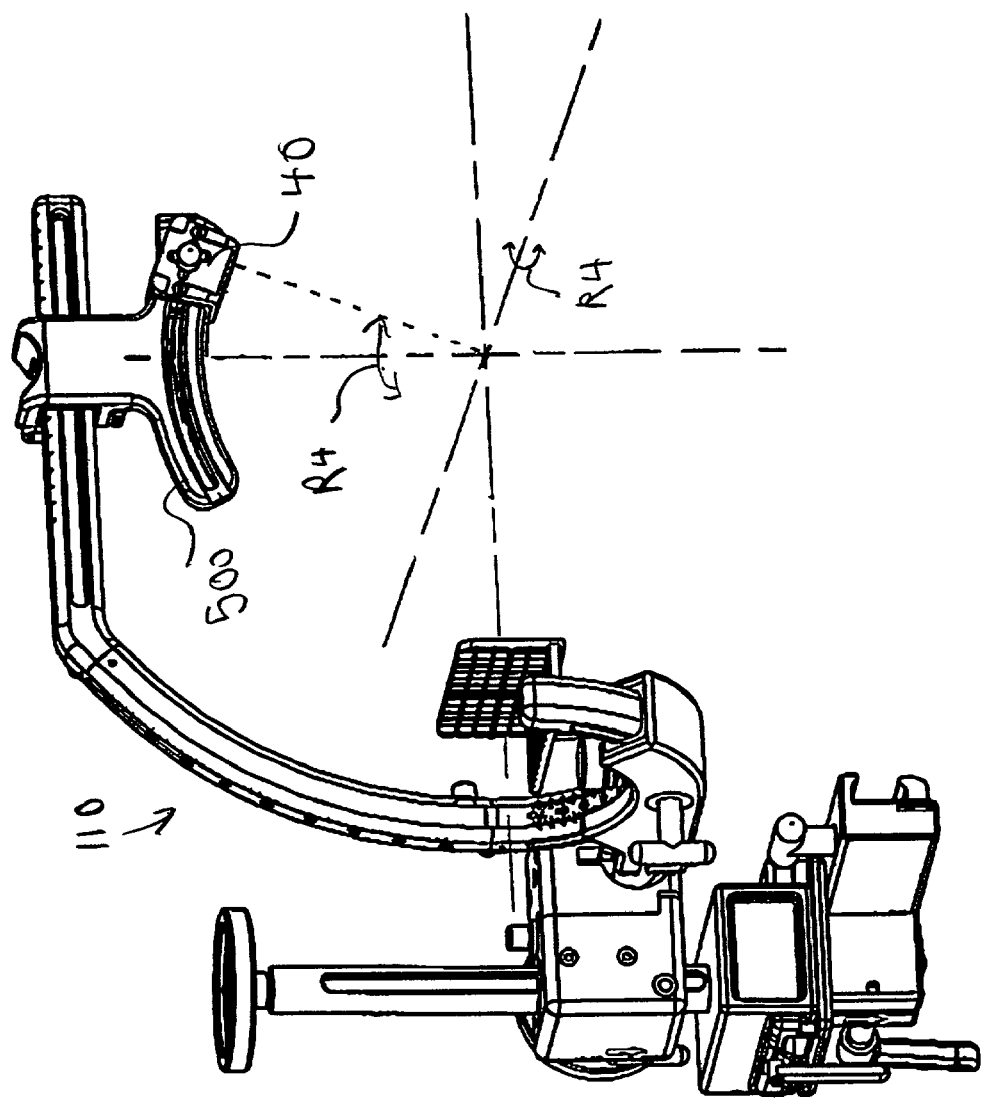

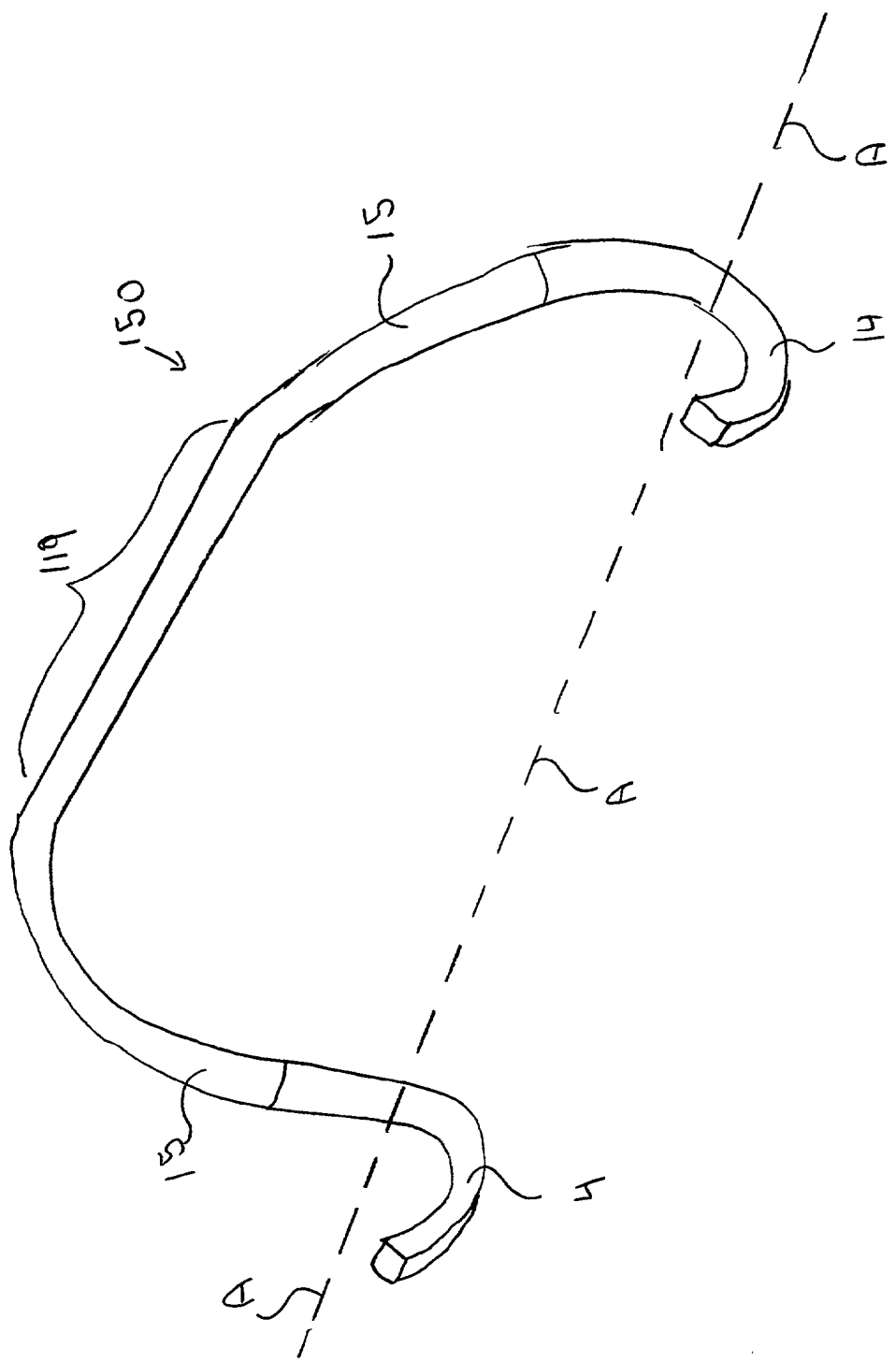

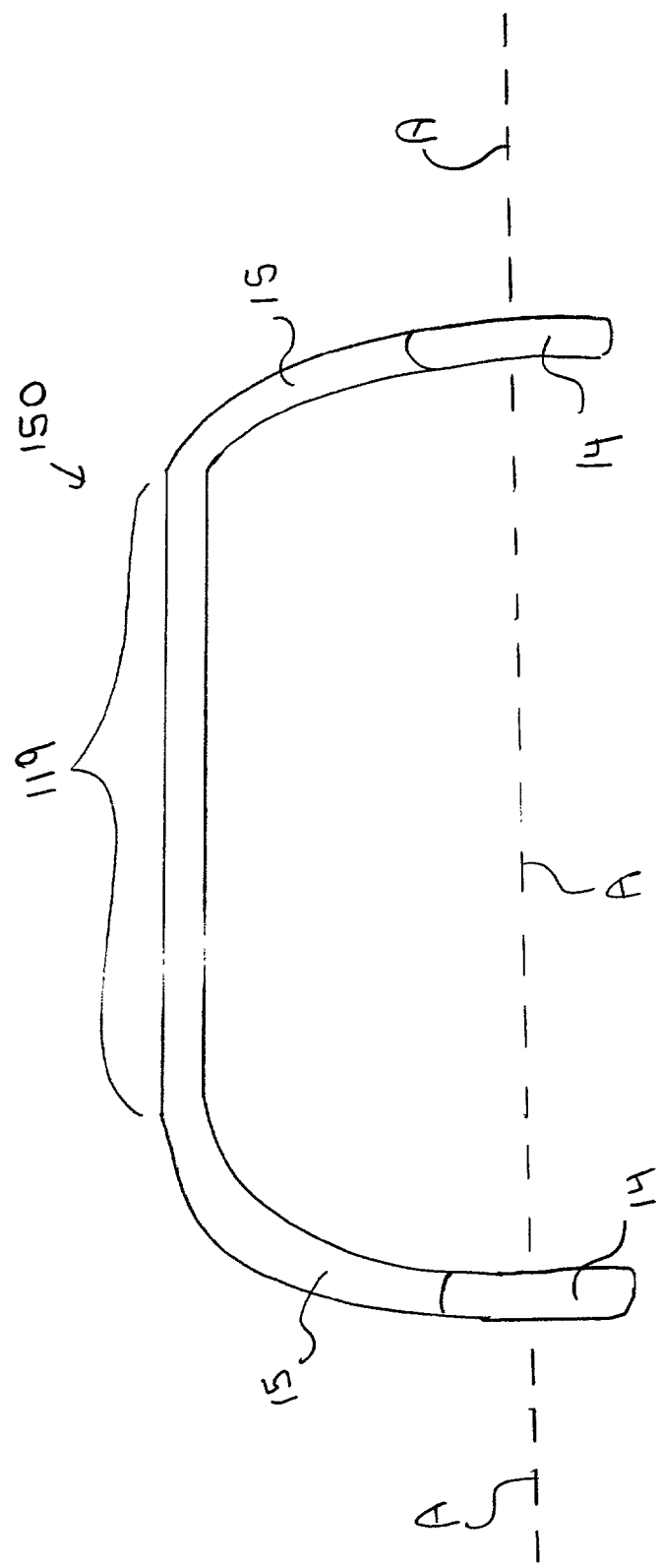

POLAR COORDINATE SURGICAL GUIDEFRAME

CROSS-REFERENCES TO RELATED APPLICATIONS

This application is a continuation of, and claims the benefit from provisional application No. 60/213,730 filed Jun. 22, 2000 and 60/226,781 filed Aug. 21, 2000, the full disclosure of which is incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

1. Technical Field

The present invention relates to surgical instrument targeting and guidance systems. In preferred aspects, the present invention relates to targeting and guidance systems for spinal surgery instrumentation.

2. Background

When performing minimally invasive percutaneous spinal surgery on a prone lying patient (such as when accessing the patient's intervertebral area for the insertion of intervertebral inserts or performing a discectomy) the various necessary surgical tools and/or inserts should preferably access the patient's spine in a posterolateral approach which is co-planar to the intervertebral plane passing between two selected adjacent vertebrae. Maintaining accurate positioning and guidance of surgical tools in this intervertebral plane has proven quite difficult to achieve in practice. Such positioning difficulties are further complicated by the fact that the intervertebral plane passing between any two adjacent vertebrae will be unique to that pair of adjacent vertebrae. This is due to natural lordotic spinal curvature, sagittal plane variances as well as coronal plane variances.

The problems encountered in positioning surgical tools in preferred orientations are not limited to positioning tools with respect to a patient's intervertebral space. Rather, it has proved difficult to position surgical tools with respect to many other locations in the body. Accordingly, what is desired is a surgical guideframe which is particularly well suited to quickly and easily position one or more surgical instruments at a selected location with respect to the patient. Most preferably, what is desired is a surgical instrument positing system which suspends one or more surgical instruments at a preferred orientation in space such that the instrument(s) can be directed in a preferred path towards a target tissue. Specifically, such a system would be adapted to quickly and easily position a surgical instrument both within a selected plane passing through the patient and at a selected angle within the selected plane.

BRIEF SUMMARY OF THE INVENTION

The present invention provides a polar coordinate surgical guidance platform for positioning one or more surgical instruments in a desired plane passing through the patient's body. As such, the surgical instrument(s) can be directed or targeted at a selected angle in a path towards a preferred target point, target tissue or surgical location.

Whereas the present invention may be used to position surgical instrument(s) such that it points towards a desired target point from a desired angle, (i.e.: is positioned at a preferred angle within in any desired plane), the present invention is particularly well suited to position the surgical instrument(s) in an intervertebral plane which passes between two adjacent vertebrae in the patient's spine. As such, the surgical instrument(s) can be held at a preferred angle while advanced in a percutaneous cannulated approach towards the patient's intervertebral space.

An advantage of the present invention is that it can be used to support operating cannulae in the preferred intervertebral plane passing between any two selected vertebrae such that various surgical instruments and/or intervertebral inserts can be passed through the cannulae and into the patient's intervertebral space in preferred posterolateral approaches, such as when performing spinal surgery. It is to be understood, however, that the present invention is not limited to systems for positioning operating cannulae. Rather, the present guideframe can be used to position any surgical instrument with respect to a patient. Accordingly, the present guideframe can be used in non-minimally invasive applications wherein it is used to position a surgical instrument in an open surgical procedure.

In one preferred aspect of the present invention, a surgical instrument positioning system comprising a pair of supports with a cross member extending therebetween is provided. In this aspect of the invention, the center portion of the cross member is preferably curved so as to form a half-circle arch over the patient. This half-circle need not have a constant radius of curvature. Rather, the radius of curvature of the half-circle arch may change along its length (i.e.: across the patient). Such variable curvature may be beneficial when accommodating the curvature of an actual patient's body. In preferred aspects, the cross member has opposite curved ends which are preferably curved in a direction perpendicular to the plane in which the center portion of the cross member is disposed. In this aspect of the invention, the supports hold the cross member such that the cross member can be rotated about an axis extending through the centers of curvature of the curved end portions of the cross member.

In an alternate aspect of the invention, the surgical instrument positioning system comprises a single support which supports a curved cross member extending over a patient. Preferably, the support is positioned to one side of a prone lying patient with a free end of the cross member extending over the back of the patient. In this aspect of the invention, the center portion of the cross member is preferably curved so as to form a quarter-circle arch over the patient. In a preferred aspect, the cross member has a curved end portion which is preferably curved in a direction perpendicular to the plane in which the center portion of the cross member is disposed. In this aspect of the invention, the support holds the cross member such that the cross member can be rotated about an axis extending through the center of curvature of the curved end portion of the cross member. In this aspect of the invention, the opposite (free) end of the cross member may preferably comprise a straight portion which is positioned in a path parallel to the axis extending through the center of curvature of the curved end portion of the cross member. It is to be understood, however, that the opposite (free) end of the cross member need not be straight. Rather, it may be curved (with a radius of curvature the same or different from that of the center curved portion of the cross member). In addition, the end of the cross member opposite to the curved and portion may instead extend to a distance such that it rests on the surgical table or directly on the patient.

The present invention also provides a surgical instrument positioning system, comprising at least one support, a cross member having at least one curved end portion, the at least one curved end portion being held by the at least one support such that the cross member is rotatable about an axis extending through a center of curvature of the at least one curved end portion of the cross member and at least one surgical instrument holder suspended from the cross member.

In preferred aspects, movement of the surgical instrument holder along the length of the curved section of the cross member results in rotation of the surgical instrument holder about a point disposed on the axis passing through the center of curvature of the at least one curved end portion of the cross member.

In preferred aspects, the surgical instrument holder is dimensioned to position a surgical instrument in a plane along which the axis extending through the center of curvature of the at least one curved end portion of the cross member passes.

In preferred aspects, the at least one support comprises a curved sleeve and wherein the at least one curved end portion of the cross member is slidably positionable within the curved sleeve.

In various preferred aspects, an alignment target may be attached to one of the at least one curved end portions of the cross member. This alignment target preferably assists the operator in aligning the guideframe to a selected plane in the patient's body. Specifically, the operator first selects the desired plane (such selection may be made while viewing an image through the patient) and then the operator aligns the guideframe to the desired plane. In preferred aspects, the operator first views an image in a path disposed along the selected plane and then aligns the axis extending through the center of curvature of the at least one curved end portion of the cross member with the viewed path. Thereafter, the cross member is rotated about the axis extending through the center of curvature of the at least one curved end portion of the cross member such that a surgical instrument holder suspends a surgical instrument within the selected plane. Such positioning is facilitated by the fact that the surgical instrument holder is dimensioned to position a surgical instrument in a plane along which the axis extending through the center of curvature of the at least one curved end portion of the cross member passes.

The alignment target (attached to the curved end portion of the cross member) preferably indicates the position of the axis about which the cross member is rotated (i.e.: the axis extending through the center of curvature of the at least one curved end portion of the cross member). In addition, the alignment target preferably also indicates the position of the plane in which the surgical instrument holder holds a surgical instrument. Accordingly, the cross member can first be aligned such that the axis extending through the center of curvature of the at least one curved end portion of the cross member is aligned, and then the cross member can be rotated about this axis to a position at which the plane in which the surgical instrument holder holds a surgical instrument is aligned with the selected plane.

In alternate aspects, one or two laser alignment source(s) may be attached to the curved end portion(s) of the cross member. Such laser sources is(are) preferably positioned so as to emit a laser beam along the axis extending through the center of curvature of the at least one curved end portion of the cross member. Accordingly, after a C-arm image intensifier has been positioned to view an image of the patient (i.e.: in a path along the selected plane), the cross member can then be aligned to the C-arm image intensifier. Specifically, the cross member can be moved to a position such that the laser beam emitted by the laser alignment source(s) is(are) aligned with the centers of the emitter and receiver of the C-arm image intensifier. In preferred aspects, the laser sources emits a planar laser beam in two intersecting planes with one of the planes being the plane in which the surgical instrument holder suspends a surgical instrument. Most preferably, the two intersecting planes of laser light intersect along the axis passing through the center of curvature of the curved end portion(s) of the cross member.

In other alternate aspects, a pair of radiopaque markers (disposed on opposite ends of the cross member) may be used to align the axis extending through the centers of curvature of the curved end portions of the cross member with the C-arm image intensifier.

The present invention also provides a method of positioning a surgical instrument in a selected plane passing through a patient's body, comprising: positioning a patient under a cross member having a curved section which spans between two supports on either side of the patient, the cross member having opposite curved ends which are disposed in planes which are perpendicular to the curved center section, the opposite curved ends each being supported by one of the supports; adjusting the position of the cross member such that an axis passing through the centers of curvature of the opposite ends of the cross member also passes through a surgical target region on the selected plane; adjusting the position of the cross member such that a plane disposed parallel to the curved center section of the cross member is disposed in the selected plane; and adjusting the position of a surgical instrument holder suspended from the cross member such that a surgical instrument suspended in the surgical instrument holder is positioned at a preferred angle in the selected plane.

The present invention also provides a method of positioning a surgical instrument in a selected plane passing through a patient's body, comprising: positioning the patient under a cross member having a surgical instrument holder suspended therefrom, the cross member having a curved end portion which is held by a support such that the cross member is rotatable about an axis extending through the center of curvature of the curved end portion of the cross member, the surgical instrument holder being positioned to hold a surgical instrument in a plane in which the axis extending through the center of curvature of the curved end portion of the cross member is disposed; adjusting the position of the cross member such that the axis extending through the center of curvature of the at least one curved end portion of the cross member is disposed in the selected plane; and rotating the cross member about the axis extending through the center of curvature of the at least one curved end portion of the cross member such that the plane in which the surgical instrument is held is aligned with the selected plane.

In addition, the present invention comprises selecting the orientation of the surgical instrument within the selected plane, thereby positioning the surgical instrument in a preferred path with respect to a target point or target tissue. In various aspects, this may be achieved by adjusting the position of the surgical instrument holder along the length of the cross member (when the curved center section of the cross member has been positioned parallel to the parallel to the selected plane).

In preferred aspects, adjusting the position of the cross member such that the axis extending through the center of curvature of the at least one curved end portion of the cross member is disposed in the selected plane comprises: viewing an image of the patient with a C-arm image intensifier in a direction along the selected plane; and aligning the cross member to the C-arm image intensifier.

In various aspects, aligning the cross member to the C-arm image intensifier may comprise emitting a laser beam from a laser source attached to cross member; and then aligning the laser beam with a target on the C-arm image intensifier; or, emitting a laser beam from a laser source attached to the C-arm image intensifier; and then aligning the laser beam with a target attached to the cross member (wherein the target indicates the position of the axis extending through the center of curvature of the at least one curved end portion of the cross member). It is to be understood that the present alignment systems are not limited to C-arm image intensifiers, but may also be used with any sort of image intensifier adapted to take a view through a patient in a preferred path.

In one aspect of the invention, two cannulae are separately positioned posterolaterally on the same or opposite sides of the patient. A further advantage of the present invention is that, when separately positioning two operating cannulae (with first and second surgical instruments passing therethrough), it enables the simultaneous positioning of first and second surgical instruments both with respect to one another and also with respect to the patient's spine such that each surgical instrument can be advanced through the cannulae into the patient in opposite posterolateral angles of approach while the surgical instruments remain in the same selected plane passing between the patient's vertebrae.

In one aspect of the invention, a surgical instrument positioning system is provided comprising a pair of supports with a cross member extending therebetween. The cross member has a curved semi-circular center section which spans between the supports. The cross member preferably has opposite curved end portions which are both curved such that they are disposed in planes which are perpendicular to the plane in which the curved center section of the cross member is disposed.

In this aspect of the invention, the opposite curved ends of the cross member are supported by the movable supports such that the cross member is rotatable about an axis passing through the centers of curvature of each of the opposite curved ends of the cross member. At least one surgical instrument holder is suspended from the cross member such that the distal end of an elongated surgical instrument (for example, an operating cannula) suspended therein will remain positioned at, or near, or pointing towards, the axis passing through the centers of curvature of each of the opposite ends of the cross member. As will be explained, the distal end of the elongated surgical instrument will remain positioned at, or close to, the same point in space as the cross member is rotated about the axis passing through the centers of curvature of each of the opposite ends.

In another aspect of the invention, the center section of the cross member comprises a quarter-circular member which may be used to support an operating cannulae (or other surgical instrument(s)) from a location disposed on one side of the patient.

In this aspect of the invention, a surgical instrument positioning system is provided comprising a single support holding the cross member (such that the cross member can be rotated about an axis passing through the center of curvature of the curved end portion of the cross member). The curved end portion of this cross member is preferably disposed in a plane which is perpendicular to the plane in which the curved quarter-circular section of the cross member is disposed. In this aspect of the invention, the cross member may further comprise a straight "free" end portion extending from the curved quarter-circular center section in a direction parallel to the axis passing through the center of curvature of the curved end portion of the cross member.

Various systems are provided for aligning the cross member such that a surgical instrument holder positioned thereon suspends a surgical instrument in a plane which is selected by the operator. Specifically, such systems provide for positioning the cross member in alignment with an image taken with an image intensifier, for example, a C-arm image intensifier.

In preferred aspects, such alignment system may include radiopaque markers disposed at opposite curved end portions of the cross member, one or more laser sources disposed at one curved end portion of the cross member (when the cross member has only one curved end portion), or at opposite curved end portions of the cross member (when the cross member has a pair of opposite curved end portions), or one or more laser sources disposed on the emitter and receiver ends of a C-arm image intensifier with an alignment target attached to the curved end portion(s) of the cross member.

In a preferred alignment system comprising radiopaque markers, such radiopaque markers may comprise height and lordotic angle markers which are attached to opposite curved ends of a semi-circular cross member. Such markers may preferably be aligned with the patient's intervertebral space (or any other selected line or plane through the patient's body) by an operator. The cross member may preferably be rotated about the axis passing through the centers of curvature of the opposite ends of the cross member (which also passes through the height and lordotic angle markers) such that the plane in which the curved center portion of the cross member is disposed is positioned parallel to the patient's intervertebral plane, (and such that a surgical instrument holder suspended from the cross member holds a surgical instrument coplanar with the patient's intervertebral plane). This may be accomplished by aligning the lordotic angle marker with the patient's intervertebral plane.

In alternate aspects, laser alignment systems are provided to align one or both ends of the cross member (i.e.: one or both of the curved end portions of the cross member) with an image intensifier. Such systems may comprise one or more lasers mounted to the curved end portions of the cross member directing laser beams onto a C-arm image intensifier or one or more lasers mounted to the C-arm directing laser beams unto a target attached to the curved end portions of the cross member.

It is to be understood that the present invention can be used to align surgical instrument(s) with any desired plane through the patient's body, and not just the patient's intervertebral plane. Such other planes may comprise any plane which can be viewed with reference to bony structures in the patient's body. All that is required is that the operator aligns the radiopaque markers with bony structures in the patient's body, preferably as viewed by a radio-image or align a laser beam passing between the C-arm and the guideframe cross member.

In further aspects of the invention, the surgical instrument holder(s) are slidably movable along the cross member and the surgical instrument is of a length such that the distal end of the surgical instrument (when positioned in the surgical instrument holder) remains positioned at, or near, or points towards, the same position in space as the surgical instrument holder(s) are slidably moved along the cross member. This aspect of the invention is particularly useful in positioning the surgical instrument(s) in a preferred path pointing towards a target tissue. Accordingly, to target a surgical region or target tissue, rotation of the guideframe about the axis passing through the center of curvature of its end portion(s) positions the surgical instrument in a preferred plane, and, movement of the surgical instrument holder along the cross member positions the surgical instrument at a preferred angle in the preferred plane.

By viewing a lateral radio-image through the patient, an operator is able to align the height and lordotic angle markers (or the laser beam passing between the C-arm and the cross member of the guideframe) such that the curved cross member is positioned to support the surgical instrument(s) in the patient's intervertebral plane, with the distal ends(s) of the surgical instrument(s) being positioned at, near, or pointing towards, the patient's intervertebral space.

By taking an anterior-posterior radio-image through the patient, a surgeon is also able to align the center of the curved center section of the cross member (in the case of a semi-circular cross member), or a straight end portion of the cross member (in the case of a quarter-circular cross member) over the center of the patient's spine. This is preferably accomplished by viewing a radiopaque mid-sagittal (ie: coronal) marker in the anterior-posterior radio-image through the patient. Alignment of the curved center section of the cross member either over the center of the patient, or to one side of the patient, assists in positioning the surgical instrument(s) to point towards the center of the patient's spine.

After the cross member has been aligned such that the axis passing through the center(s) of curvature of its curved end portion(s) also passes along a path along the selected plane, the distal end of a surgical instrument positioned within the surgical instrument holder will remain at or near a point on the path in the selected plane. For example, should such point comprise a point positioned within a the patient's intervertebral space, the distal end of a surgical instrument positioned within the surgical instrument holder will remain at or near, the patient's intervertebral space. Advantageously, the surgical instrument will then point towards the intervertebral space both: (1) as the cross member is moved (ie: rotated) with respect to the support(s), and (2) as the surgical instrument holders are moved around the circumference of the cross member to various preferred locations.

To assist in positioning the cross member, the support(s) is(are) preferably separately positionable both in a vertical direction and in a cephal-caudal direction on the side of the patient, with at least a portion of the supports also being positionable at least to some degree in a direction perpendicular (ie: laterally across) the patient.

BRIEF DESCRIPTION OF THE DRAWINGS

FIG. 17A is a perspective view of a semi-circular cross member guideframe having laser beam emitters positioned at its opposite curved end portions.

FIG. 17B is a perspective view of a semi-circular cross member guideframe having laser beam emitters positioned at one of its curved end portions.

FIG. 17C is a perspective view of a quarter-circular cross member guideframe having a laser source adapted to emit a laser beam in two intersecting planes.

FIG. 18A is an illustration of a laser beam alignment system emitting laser beams in two intersecting planes, with the laser beam alignment system attached to a C-arm image intensifier FIG. 18B is close up view of the a laser beam alignment system of FIG. 18A.

FIG. 19 is an illustration of the system of FIGS. 12 to 16B, showing a further degree of freedom.

FIG. 22 is a perspective view of a surgical guideframe having a straight center portion, a first pair of curved portions and a pair of curved ends.

FIG. 23 is a front elevation view of the surgical guideframe of FIG. 22.

DETAILED DESCRIPTION OF THE INVENTION

The present invention provides a surgical guideframe which is ideally adapted to support and align one or more surgical instrument(s) at a preferred location within a desired plane, for example, an intervertebral plane passing through a patient's intervertebral space at a lordotic angle. An advantage of the present system is that one or more surgical instruments can easily be positioned in a preferred path, thereby targeting a preferred tissue location. One particularly advantageous application of the present system is that it can be used to position one or more surgical instruments in desired posterolateral angles with respect to the patient (while remaining in the patient's intervertebral plane) during minimally invasive spinal surgery.

Various embodiments of the present surgical guideframe are presented. Specifically, a first embodiment is seen in FIGS. 1 to 4, 6, 8 and 9 and a second embodiment is seen in FIGS. 12 to 16B and 19. The first embodiment comprises a semi- or generally half-circular cross member supported at each end by movable supports and the second embodiment comprises a hemi- or quarter-circular cross member supported at only one end by a movable support. The illustrations of various components shown in FIGS. 5, 7, and 10 to 11, 20 and 21 may apply to either embodiment of the present surgical guideframe. In addition, the various alignment systems shown in FIGS. 17A to 18C may apply to either embodiment of the present surgical guideframe. The surgical guideframe of FIGS. 22 and 23 incorporates features of both embodiments of the guideframe design.

Figure 1:
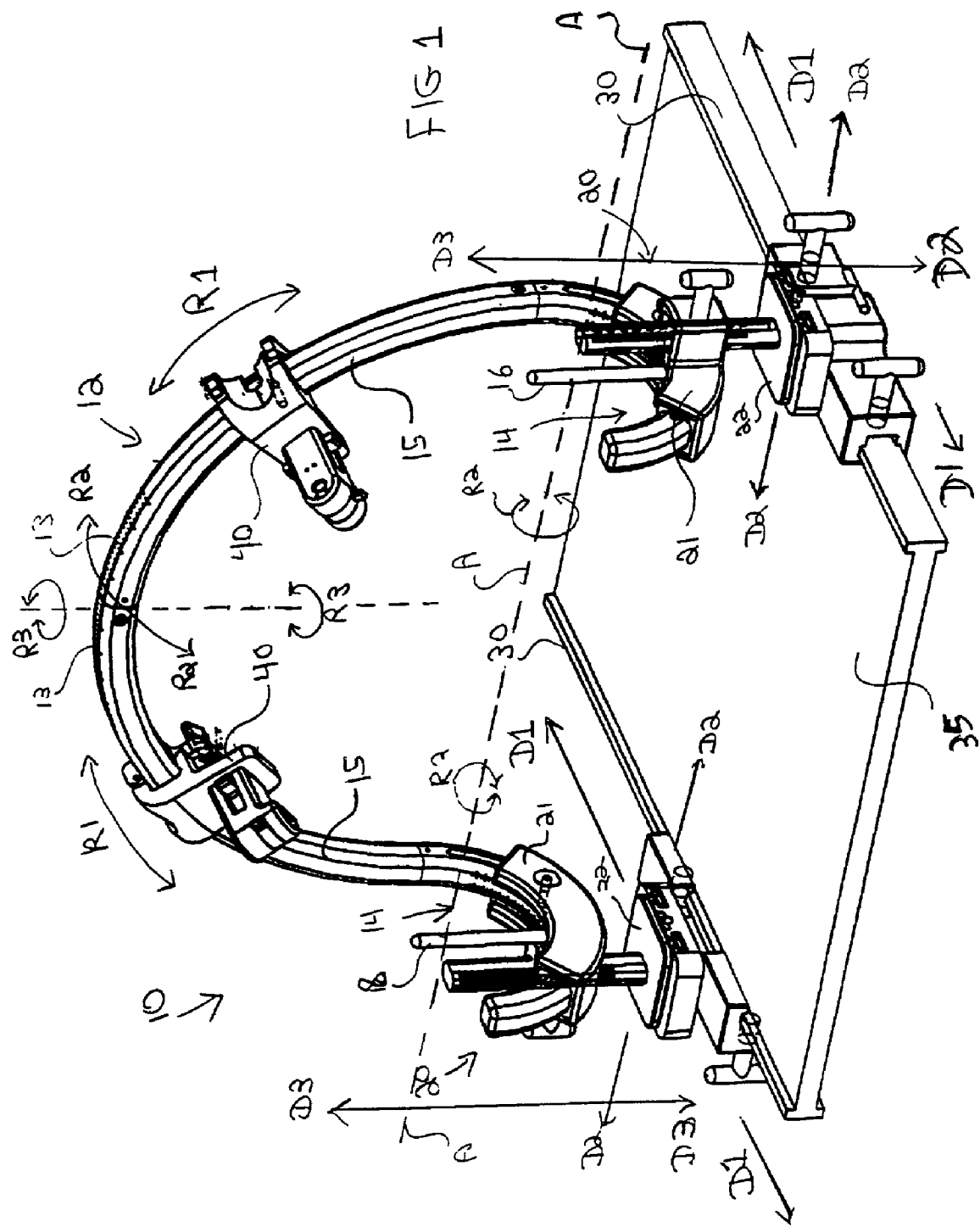
FIG. 1 is a front perspective view of a first (semi-circular) embodiment of the present polar coordinate surgical guideframe.

Referring first to FIG. 1, a guideframe 10 is provided. Guideframe 10 comprises a curved cross member 12 supported at its opposite curved ends 14 by a pair of supports 20, as shown. Supports 20 are preferably adapted to be separately positionable back and forth in directions D1. Directions D1 correspond to a cephal-caudal (head-toe) direction with respect to a patient lying therebetween, as will be explained. In a preferred aspect, supports 20 are adapted to be slidably positionable to various locations along guide rails 30 (which are disposed on opposite sides of a patient lying therebetween). In a most preferred aspect of the invention, guide rails 30 are coupled directly to, (or formed integrally with), an operating table 35 on which the patient is positioned. Alternative positioning systems for moving supports 20 in a cephal-caudal direction (including screw positioning systems) are also envisioned.

Cross member 12 is adapted to support one or more surgical instrument holders 40, which are sidably positionable therealong. Specifically, surgical instrument holders 40 can be moved around the center section of cross member 12 such that they rotate when moved in directions R1, as shown.

Figure 2:
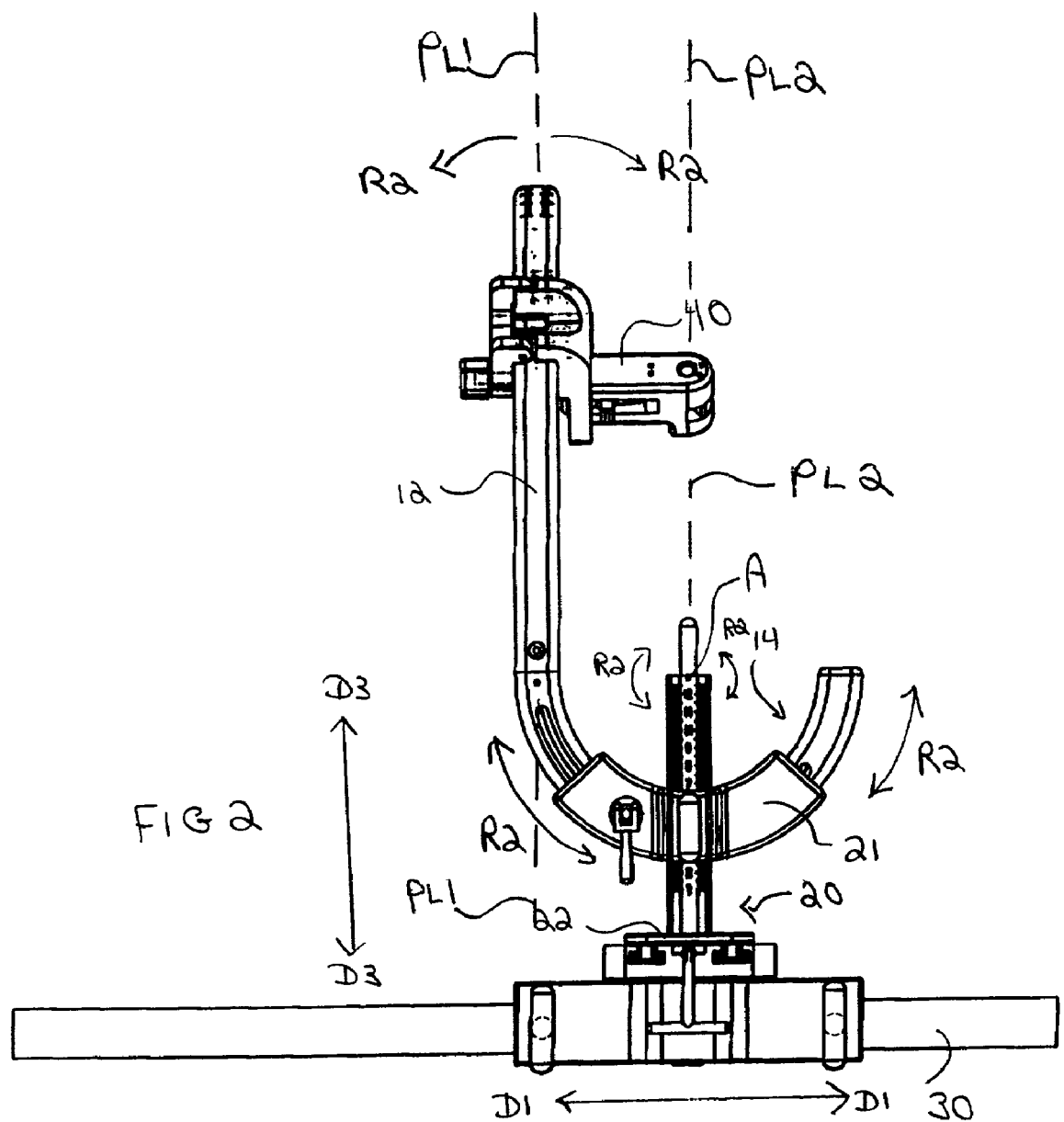
FIG. 2 is a left side elevation view of the surgical guideframe of FIG. 1.

As can be seen in FIG. 2, an advantageous feature of the present invention is that cross member 12 can be positioned (ie: tilted or rotated) in direction R2, such that cross member 12 rotates about an axis A which passes through the centers of curvature of ends 14 of cross member 12.

Returning to FIG. 1, an upper portion 22 of each of supports 20 is adapted to move back and forth laterally in direction D2 (which is perpendicular to direction D1). Accordingly, separate positioning of each of supports 20 along guiderails 30 (in direction D1) is possible, permitting rotation of cross member 12 in direction R3.

In one aspect of the invention, one curved end 14 has a height marker 16 mounted thereon, and the other curved end 14 has a lordotic angle marker 18 mounted thereon. (Further details of height marker 16 and lordotic angle marker 18 are shown in the schematic views of FIGS. 8 to 11).

Both of the radiopaque height marker 16 and the radiopaque lordotic angle marker 18 are mounted to opposite curved ends 14 of cross member 12 such that they are positioned on axis A (which extends through centers of curvature of opposite ends 14 of cross member 12). In addition, lordotic angle marker 18 preferably comprises a radiopaque wire disposed parallel to a plane in which the curved center section of cross member 12 is disposed. As will be explained, lordotic angle marker 18 is preferably co-planar with the plane (PL2 in FIG. 2) in which surgical instrument holders 40 position surgical instruments.

As seen in FIG. 2, each support 20 has a curved sleeve 21 attached thereto. Curved ends 14 of cross member 12 are received in curved sleeves 21 as shown. As curved end 14 is slidably moved to various positions in curved sleeve 21, cross member 12 can be rotated in direction R2 to various positions about axis A (which is disposed at the center of curvature of curved end portion 14). In addition, the position of curved sleeves 21 on supports 20 is also vertically adjustable in direction D3. In an optional preferred aspect, cross member 12 can be easily removed from supports 20 during a medical emergency, or whenever hands-free operation is desired.

Figure 3:
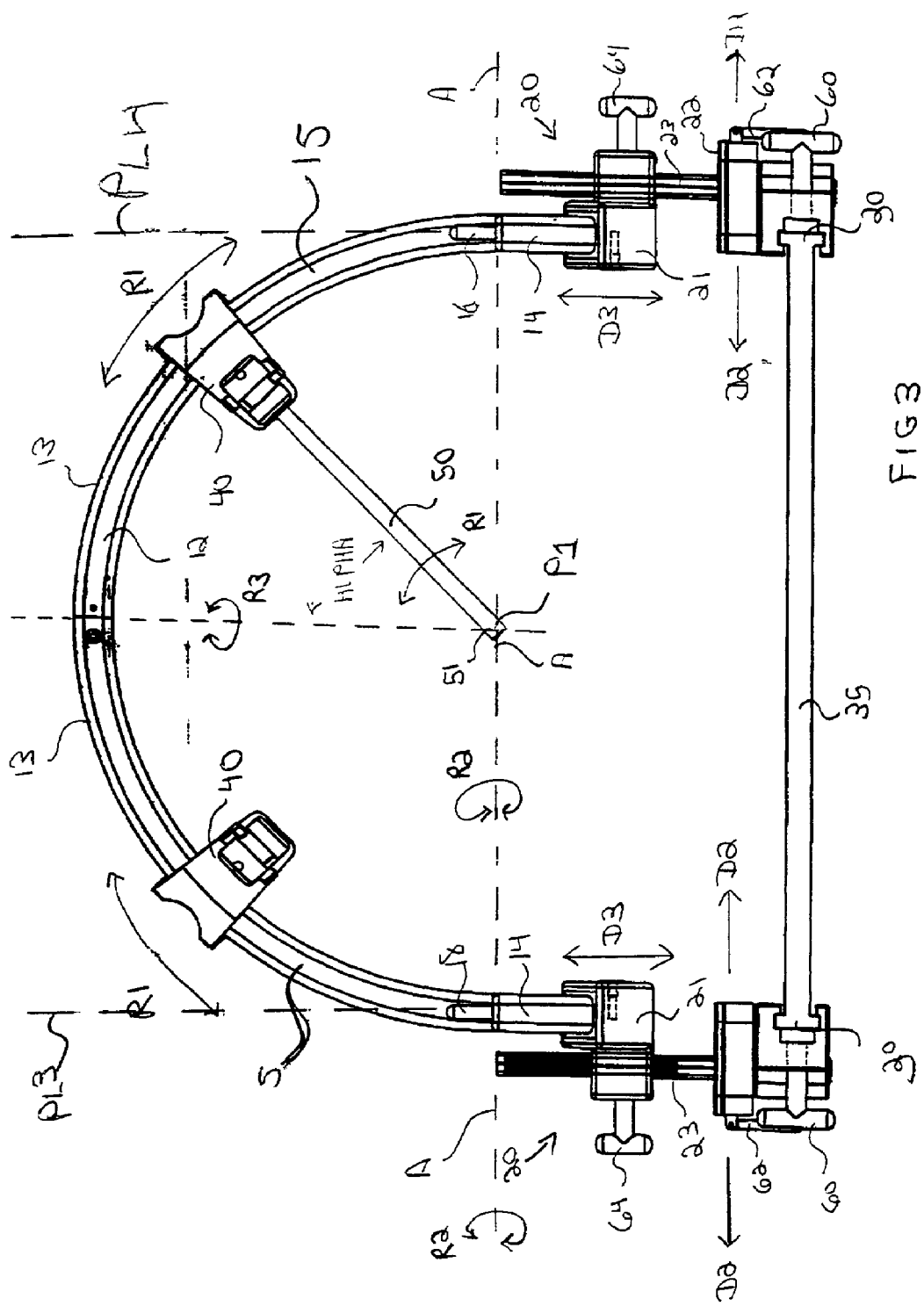
FIG. 3 is a front elevation view of the surgical guideframe of FIG. 1.

As seen in FIG. 3, an elongated surgical instrument 50 (for example an operating cannula) can be suspended from (one or more) surgical instrument holders 40 such that its distal end 51 is positioned at, near, or pointing towards, a point P1 on axis A. Accordingly, when cross member 12 is rotated either in direction R2 (FIG. 2) or R1 (FIG. 3) distal end 51 of surgical instrument 50 will remain at, near, or pointing towards point P1 on axis A. (Although FIG. 3 shows only one surgical instrument 50, it is to be understood that more than one surgical instrument holder 40 may be used, with each surgical instrument holder 40 preferably supporting one surgical instrument therein). This feature is particularly advantageous in that it permits both surgical instruments to simultaneously target the same tissue. Stated another way, both surgical instruments may easily be targeted (from different angles) to point towards the same operative site in the patient. For example, when performing spinal surgery, two operating cannulae can be used with each approaching the spine in opposite posterolateral angles.

In optional preferred aspects of the invention cross member 12 is radio-lucent, and as such, it may be made of a carbon-fiber laminate or other suitable radio-lucent material.

In additional optional preferred aspects of the invention, surgical instrument(s) may be easily removed from surgical instrument holder(s) 40, permitting hands-free operation, if desired.

Figure 4:
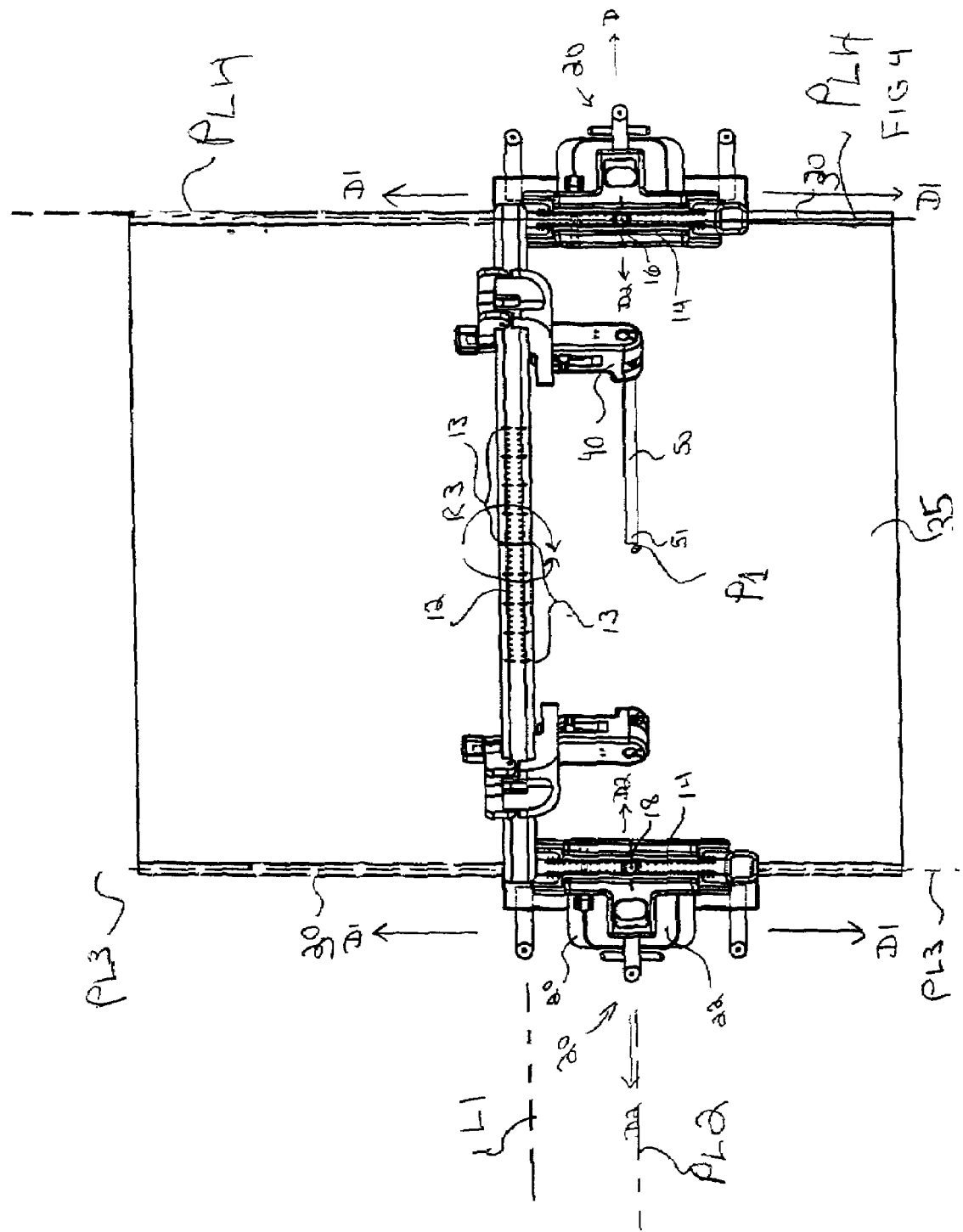
FIG. 4 is a top plan view of the surgical guideframe of FIG. 1.
Figure 5:
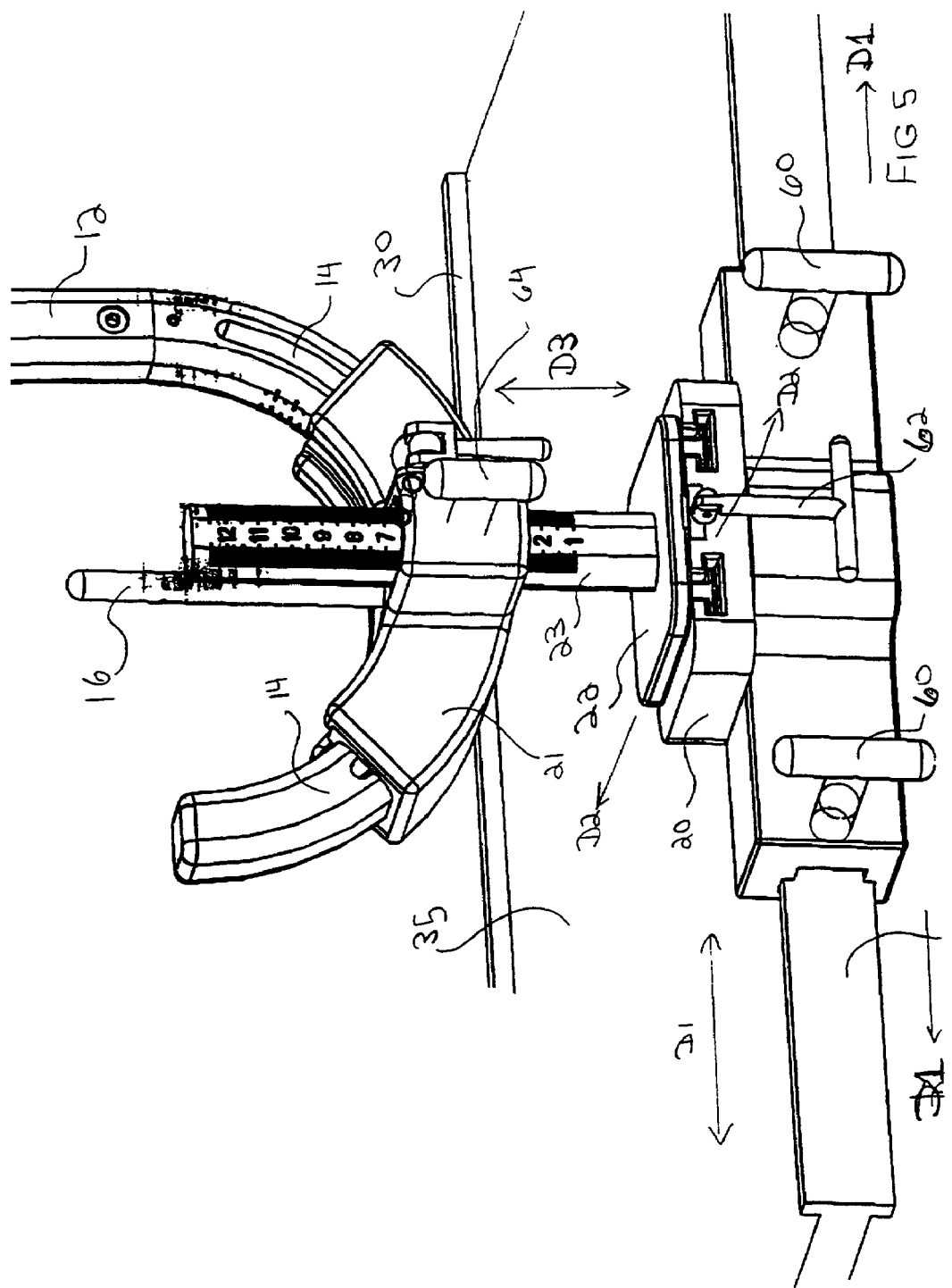
FIG. 5 is a close-up left side view of one of the supports of the surgical guideframe of FIG. 1.
Figure 6:
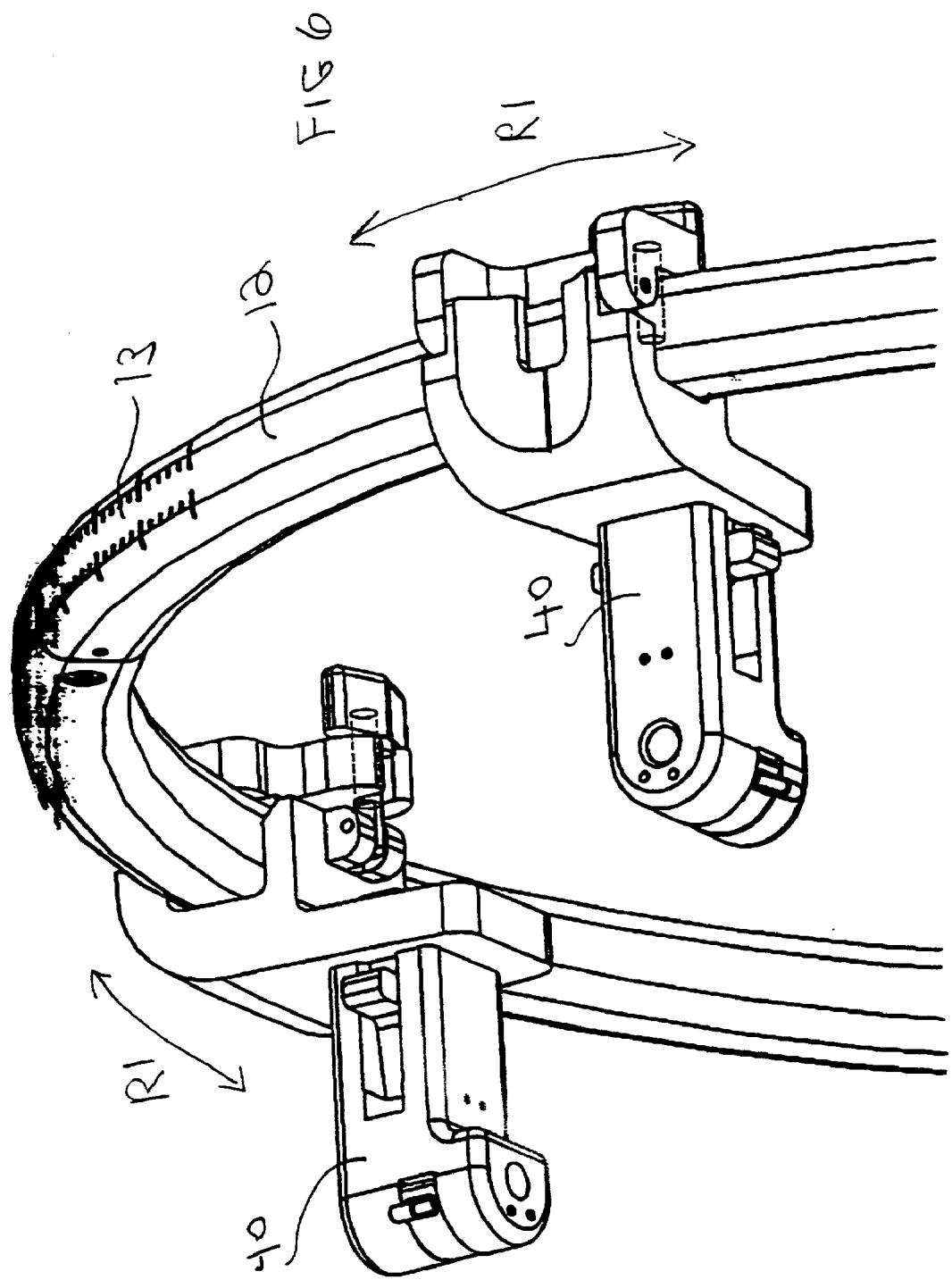
FIG. 6 is a close-up left side view of a pair of surgical instrument holders sildably attached to the cross member of the surgical guideframe.

FIGS. 4, 5 and 6 show further details of the guideframe illustrated in FIG. 1, as follows.

FIG. 4 shows indicia 13 printed on cross member 12 which are used when positioning surgical instrument 50. Therefore, a preferred angle ALPHA (see FIG. 3) for surgical instrument 50 to enter patient P can be set by adjusting the position of surgical instrument holder 40 to a preferred position along the length of cross member 12 using indicia 13. (Whereas FIG. 4 only shows indicia 13 along a center portion of cross member 12, it is to be understood that indicia 13 preferably extends along most of, or all of, the length of the curved center section of cross member 12 spanning between supports 20.)

Referring to FIG. 5, control handles 60 can be loosened to permit support 20 to be moved in direction D1, control handle 62 can be adjusted to permit portion 22 of support 20 to be moved in direction D2, and control handle 64 can be used to adjust the height of sleeve 21 on vertical member 32 of support 20.

Figure 7:
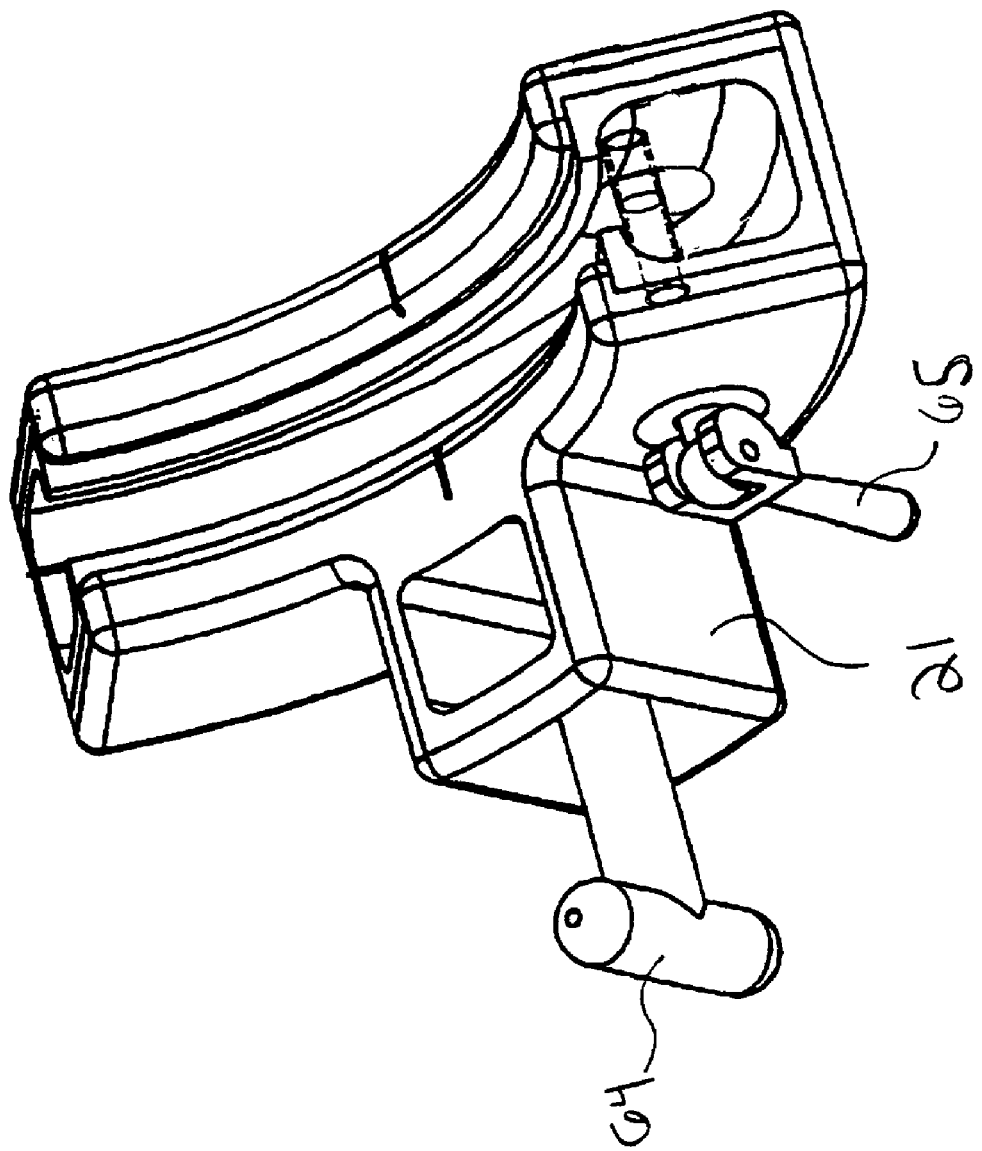
FIG. 7 is a perspective view of a curved sleeve which supports a curved end of the cross member on a support.

FIG. 7 shows details of curved sleeve 21 which supports a curved end 14 of cross member 12 on a support 20, showing control handle 64 which is used to hold onto when sliding curved sleeve 21 up and down vertical member 32 (not shown). Fastener 65 is used to lock the position of curved end 14 of cross member 12 (not shown) relative to curved sleeve 21.

As can be seen clearly in FIGS. 1, 2 and 3, surgical instrument holder 40 is positionable along the length of the curved center section of cross member 12 such that movement of surgical instrument holder 40 results in rotation about a point (P1 in FIG. 3) on the axis (i.e. axis A) which passes through the center of curvature of opposite curved end portions 14 of cross member 12. As can be seen, the center section 15 of cross member 12 is preferably disposed in a plane (PL1 in FIG. 1) which is perpendicular to the planes (PL3 and PL4 in FIG. 3) in which each of curved end portions 14 are disposed.

Accordingly, surgical instrument holder(s) 40 position a surgical instrument 50 such that it can be moved to various positions (i.e.: different angles) within plane PL2 which is parallel to plane PL1 in which curved center portion 15 of cross member 12 is disposed. Axis A (and point P1 disposed thereon) are both disposed in plane PL2. As can be seen in FIG. 3, curved ends 14 are disposed in planes PL3 and PL4. Planes PL3 and PL4 are both perpendicular to planes PL1 and PL2.

It is to be understood that the present invention also encompasses designs in which the cross member does not have a curved end portion disposed perpendicular to the plane in which the curved center portion of the cross member is disposed. For example, different systems for supporting the cross member (i.e.: avoiding curved end portions 14 and curved sleeves 21) are envisioned. As such, the present invention encompasses any such alternate support system which positions the cross member such that it can be rotated about an axis which can be aligned with a selected plane through the patient's body, wherein the surgical instrument holder is positioned such that it suspends a surgical instrument (at a preferred angle) in a plane along which the axis passes.

A particular advantage of the present system of curved sleeves 21 receiving curved end portions 14 therein is that image viewing along axis A is possible without any portions of cross member 12, (i.e.: its curved center portion 15 or its curved end portions 14) being positioned along axis A. This feature is particularly advantageous when aligning axis A with the path along which an image is viewed by an image intensifier, as will be explained.

Referring to FIG. 2, curved center portion 15 of cross member 12 is disposed in plane PL1. Surgical instrument holder(s) 40 suspend a surgical instrument such that it can be moved (to various angles) within plane PL2. PL2 is parallel to plane PL1. Accordingly, by moving surgical instrument holder 40 along curved center portion 15 of cross member 12, a surgical instrument held therein can be rotated to a preferred orientation in plane PL2.

As will be explained, a preferred method of operation of the present guideframe system is to align plane PL2 with a selected plane passing through the patient's body. As will also be explained, this preferred method of operation may also comprise aligning point P1 with a target region of tissue such that the present guideframe may be used to position surgical instrument 50 in any preferred angle in plane PL2, wherein surgical instrument 50 is directed towards point P1 within the target region of tissue.

Figure 8:
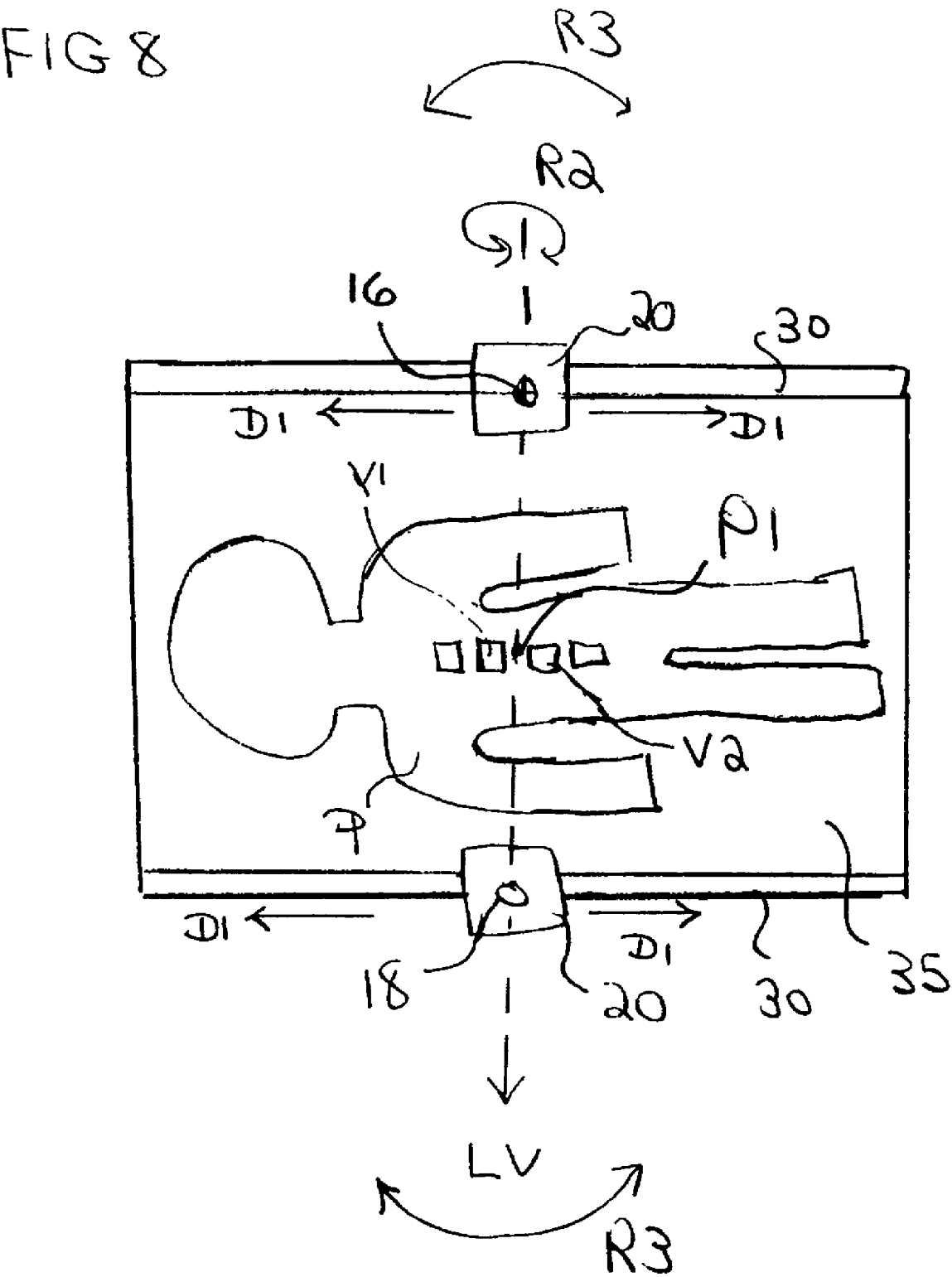
FIG. 8 is a top schematic plan view of a patient lying in a prone position on an operating table between a pair of guiderails.

FIGS. 8 to 11 detail a preferred method of using the first embodiment of the present invention as described in FIGS. 1, 2 and 3. FIG. 8 is a schematic top plan view of a patient P positioned on operating table 35, lying in a prone position between guiderails 30. An operator may first take a lateral view (having a path shown as "LV") through the patient with a C-arm image intensifier. After the operator has taken such a lateral view LV through the patient, the operator may then select a preferred plane passing through a target region of tissue. After this selection of preferred plane has been made, the operator then aligns the present guideframe to support a surgical instrument at a preferred angle within this selected plane.

Specifically, the location of a selected plane through the patient is determined. Then, the guideframe is positioned such that its axis A passes along the selected plane through the target tissue. Then, cross member 12 is rotated (about axis A) to a position such that plane PL2 is aligned with the selected plane. An advantage of the present system is that no portion of cross member 12 (i.e.: portions 14 or 15) are positioned along path LV. The an operator has a "clear view" through the patient when positioning surgical instruments to target a surgical operative site within the patient.

For example, a lateral view LV may first be taken through the patient, and a preferred intervertebral plane identified. Cross member 12 is then moved to a position such that its axis A passes through the patient along the selected plane. For example, cross member 12 may be moved by positioning supports 20 such that axis A is aligned along the path of lateral view LV through a selected intervertebral plane passing between two selected vertebrae V1 and V2. As such, the position of cross member 12 (not shown) spanning between supports 20 is adjusted by separately moving supports 20 in direction D1 such that a gap between vertebrae V1 and V2 is seen. (As such cross member 12 is rotated in direction R3).

Figure 9:
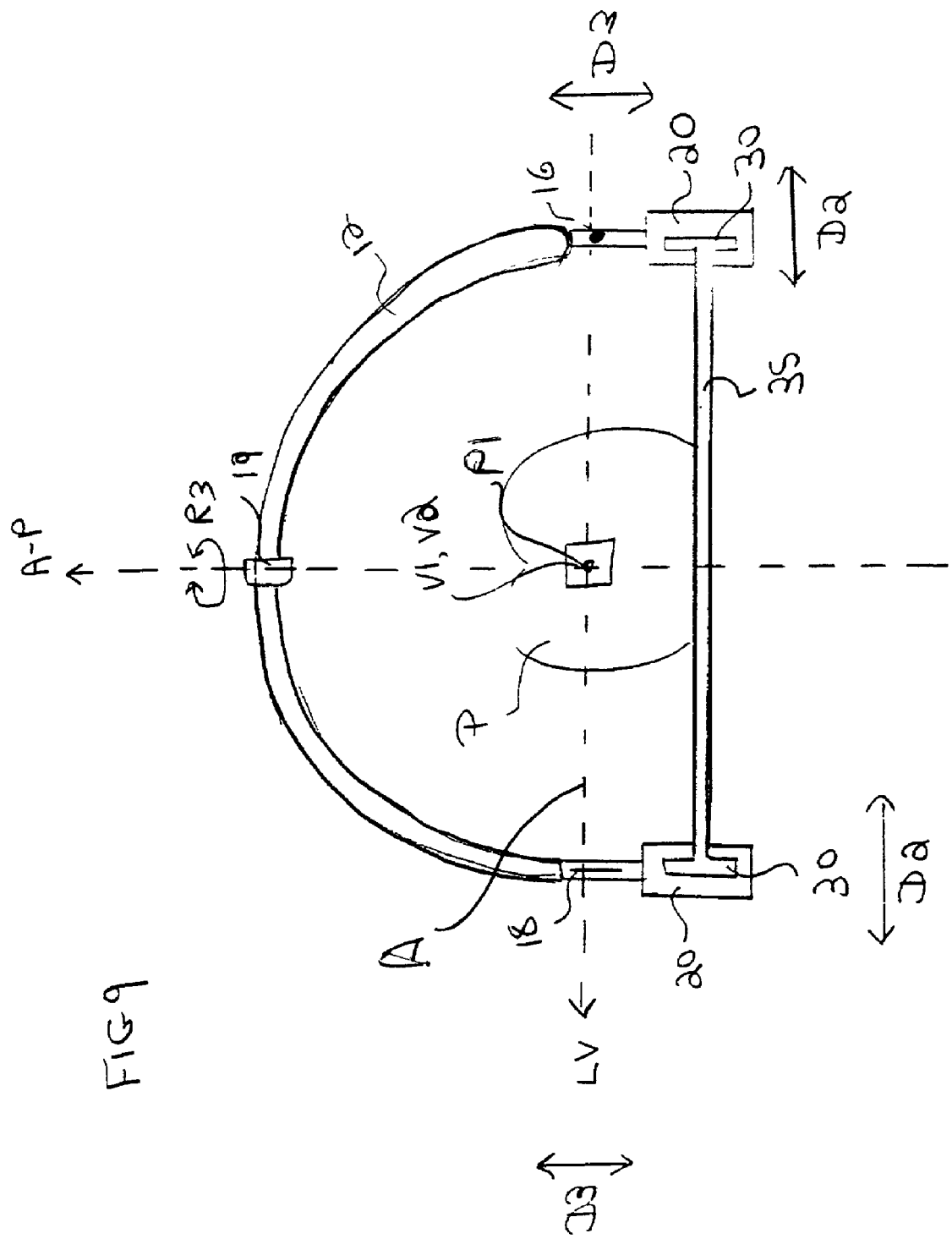
FIG. 9 is a front cross sectional elevation view of patient positioned on operating table showing the direction in which a lateral image view is taken through the patient.

FIG. 9 is a front schematic elevation view of patient P positioned on operating table 35 showing lateral view LV to which axis A (and markers 16 and 18 positioned therealong) is aligned. As can be seen, independent adjustment of supports 20 in vertical direction D3 will also assist in positioning cross member 12 (and markers 16 and 18 thereon) such that these markers are aligned with the patient's intervertebral space (ie: such that axis A is positioned to pass between vertebrae V1 and V2 in lateral view LV).

Figure 10:
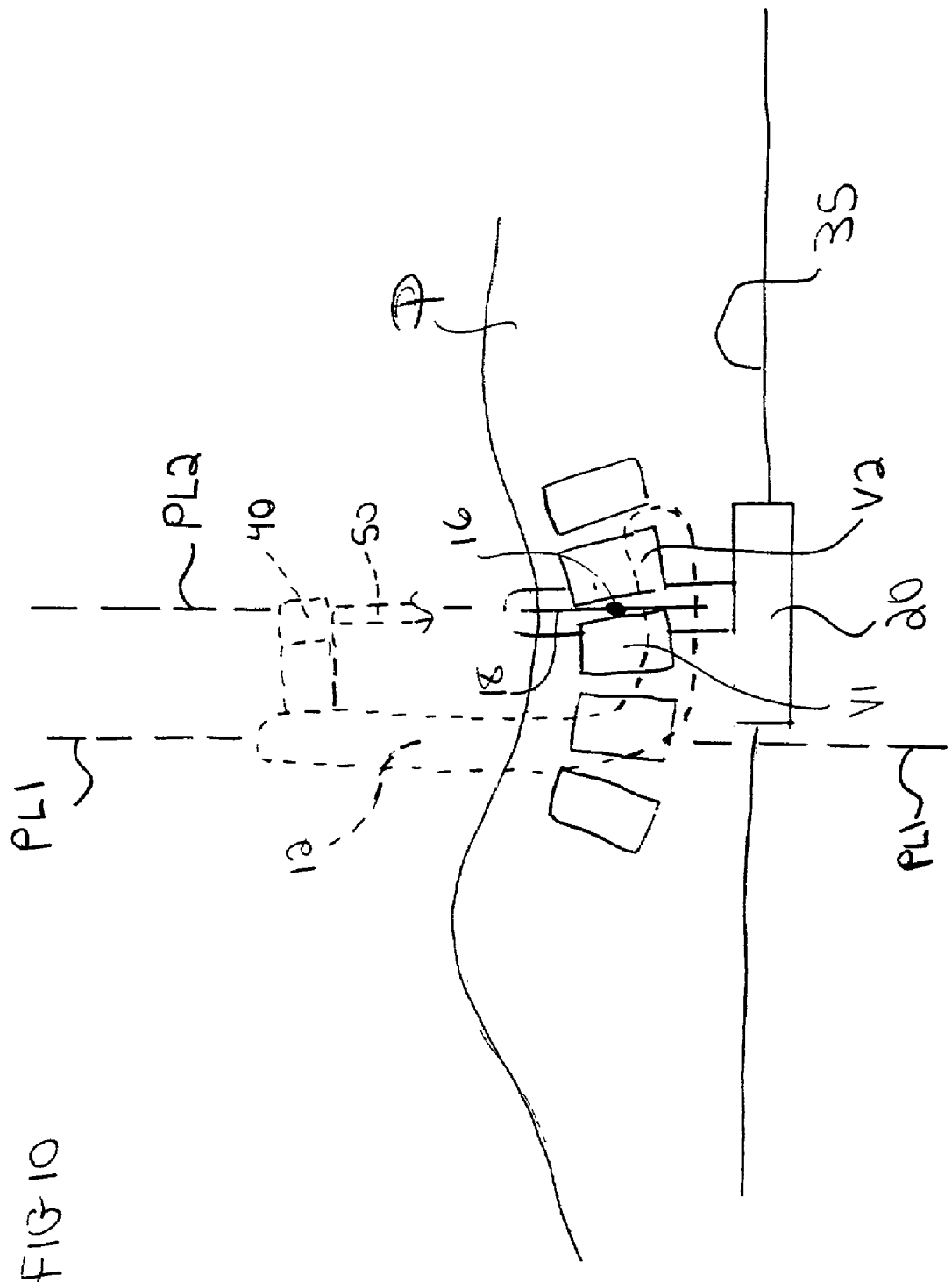
FIG. 10 is a side elevation schematic view of vertical and horizontal alignment of a pair of radiopaque markers with a patient's intervertebral space.

When lateral view LV has initially been taken, an image corresponding to that of FIG. 10 will be seen. Specifically, height marker 16 (which preferably comprises a radiopaque bead) will be seen superimposed on lordotic marker 18 (which preferably comprises a radiopaque line or wire which is disposed parallel to the plane in which the center curved section of cross member 12 is disposed).

Figure 11:
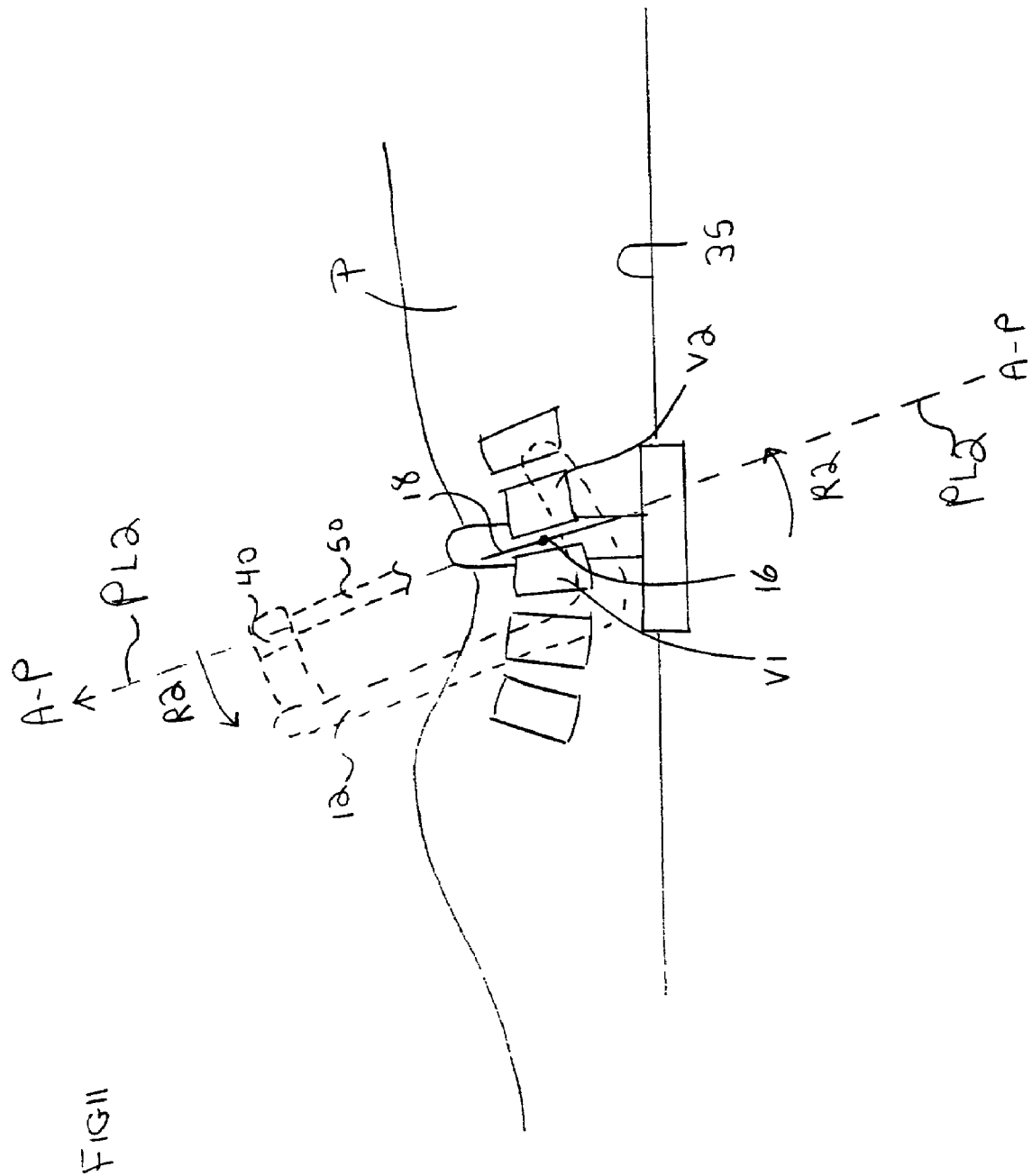
FIG. 11 is a side elevation schematic view of rotational alignment of a lordotic angle radiopaque marker with a patient's intervertebral plane.

As seen in FIG. 11, cross member 12 may then be rotated in direction R2 such that lordotic marker 18 is aligned with the selected plane (i.e.: the intervertebral plane passing between vertebrae V1 and V2). As such, surgical instrument 50 will also be positioned in the intervertebral plane.

An anterior-posterior radio-image A-P is preferably also taken through the intervertebral plane passing between vertebrae V1 and V2. This anterior-posterior radio-image A-P can be used to align a mid-sagittal (or coronal) marker (#19 in FIG. 9) positioned at the center of cross member 12 over the center of vertebrae V1 and V2. To center coronal marker 19 over the center of vertebrae V1 and V2, supports 20 are moved in direction D2 (FIG. 9).

After cross member 12 has been positioned as shown in FIG. 11, (ie: with markers 16 and 18 superimposed in a center of the patient's intervertebral space, and with the line of marker 18 passing generally evenly between vertebrae V1 and V2, and with mid-sagittal marker 19 positioned over the center of the patient's intervertebral space, or other target tissue), surgical instrument(s) 50 suspended in surgical instrument holder(s) 40 will be positioned in a plane passing generally evenly between the patient's vertebrae V1 and V2, (the patient's intervertebral plane). Thereafter, surgical instrument holder(s) 40 can be moved to desired positions along cross member 12 such that surgical instrument(s) 50 can be advanced into the patient at preferred posterolateral angles.

It is to be understood that the present invention can be used to align surgical instruments with any desired plane through the patient's body. As such, the present invention is not limited in any way to spinal applications. All that is desired in performing such alignment is that the cross member be aligned with targets (e.g.: bones or bony structures) within the patient's body. This may preferably be accomplished by viewing radio-images through the patient.

When aligning the present system with a desired plane through the patient, the height and angle markers are first preferably superimposed on top of one another and with the desired plane, and then, the cross member 12 is rotated such that the elongated angle marker 18 is coplanar with the selected or desired plane. Lastly, the system may be aligned by positioning the center of cross member 12 directly over the center of a target region in the desired plane. As such, the present invention may be used to align a surgical instrument with a patient's intervertebral plane, a plane through one of the patient's vertebrae (such as when performing a vertebroplasty) or within a "growth plate" (ie: a segment of a maturing vertebrae of a child).

FIGS. 12 to 16B and 19 illustrate a second embodiment of the present surgical instrument positioning system. The primary difference between the first and second embodiments of the present system is that the first embodiment comprises a cross member supported at two opposite ends whereas the second embodiment comprises a cross member supported at only one end.

Figure 12:
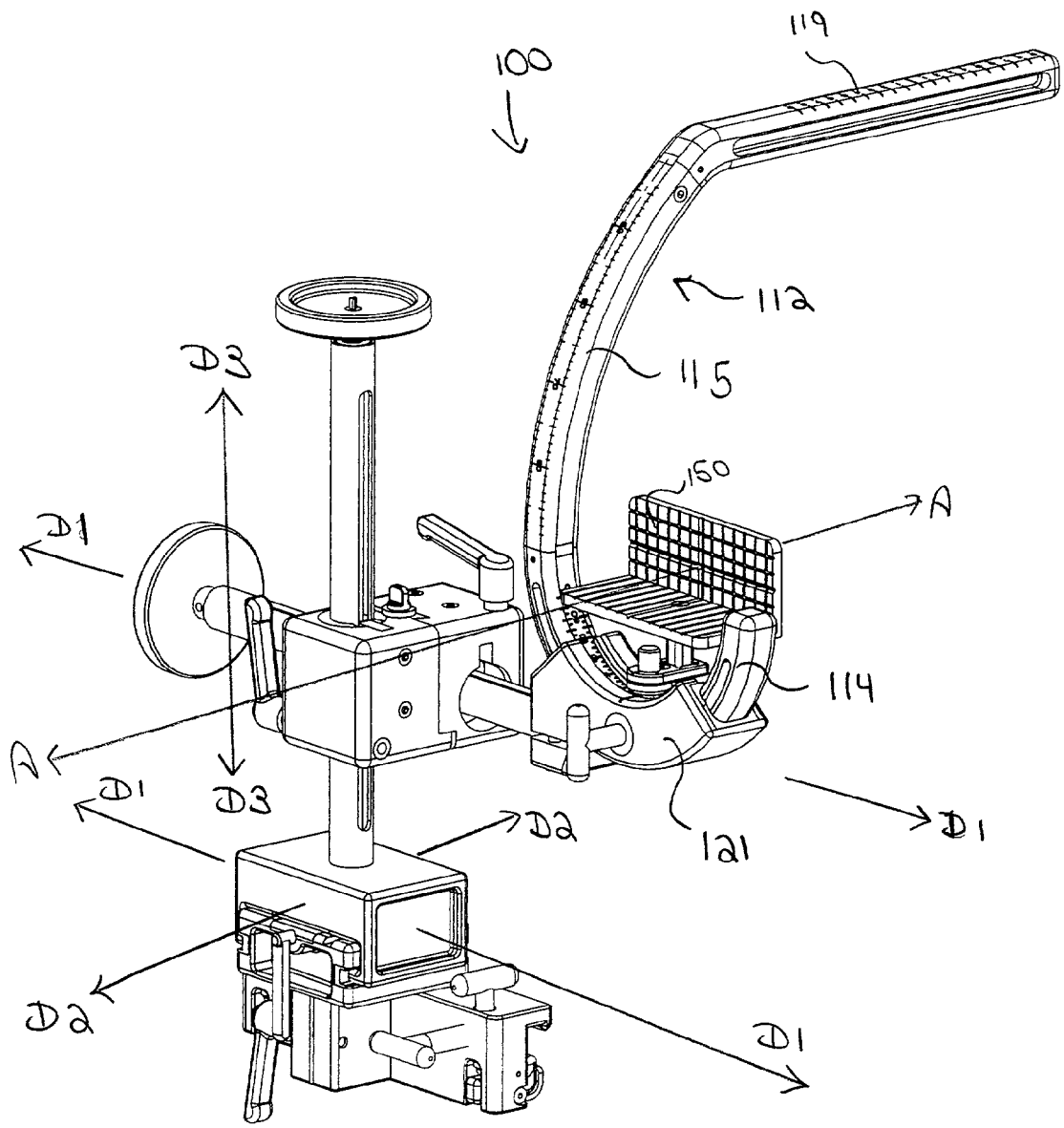
FIG. 12 is a right front perspective view of a second (quarter-circular) embodiment of the present polar coordinate surgical guideframe.
Figure 13:
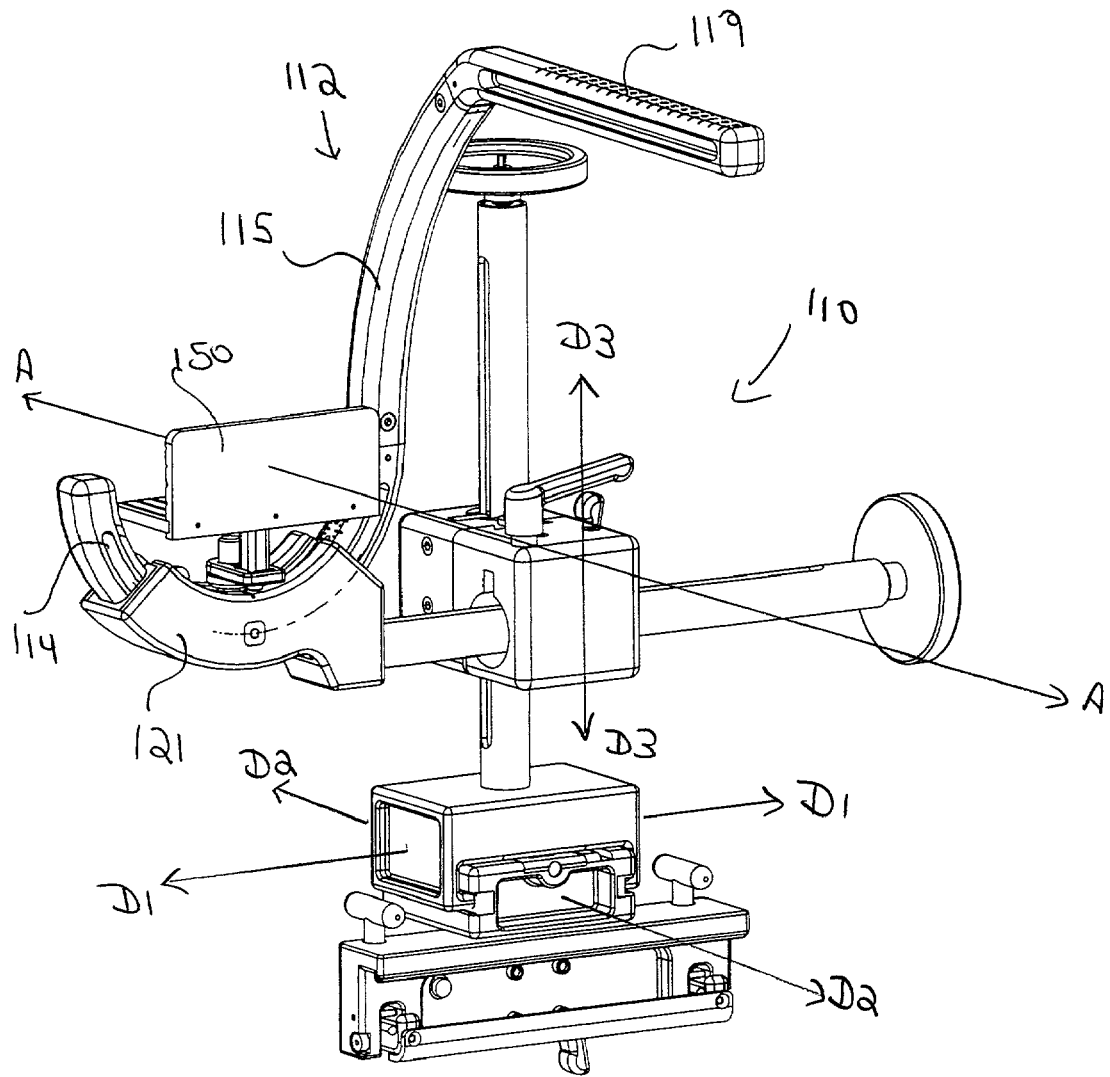
FIG. 13 is a left front perspective view of a the embodiment of the surgical guideframe of FIG. 12.

FIG. 12 illustrates a guideframe 100 comprising a center curved section 112. Preferably, center curved portion 112 is about the length and angle of a quarter circle. Attached to one end of center curved section 112 is a curved end portion 114 which is held in position within a curved sleeve 121. As is similar to the first embodiment of the guideframe, movement of curved end portion 114 within curved sleeve 121 results in rotation of cross member 112 about axis A.

Figure 14:
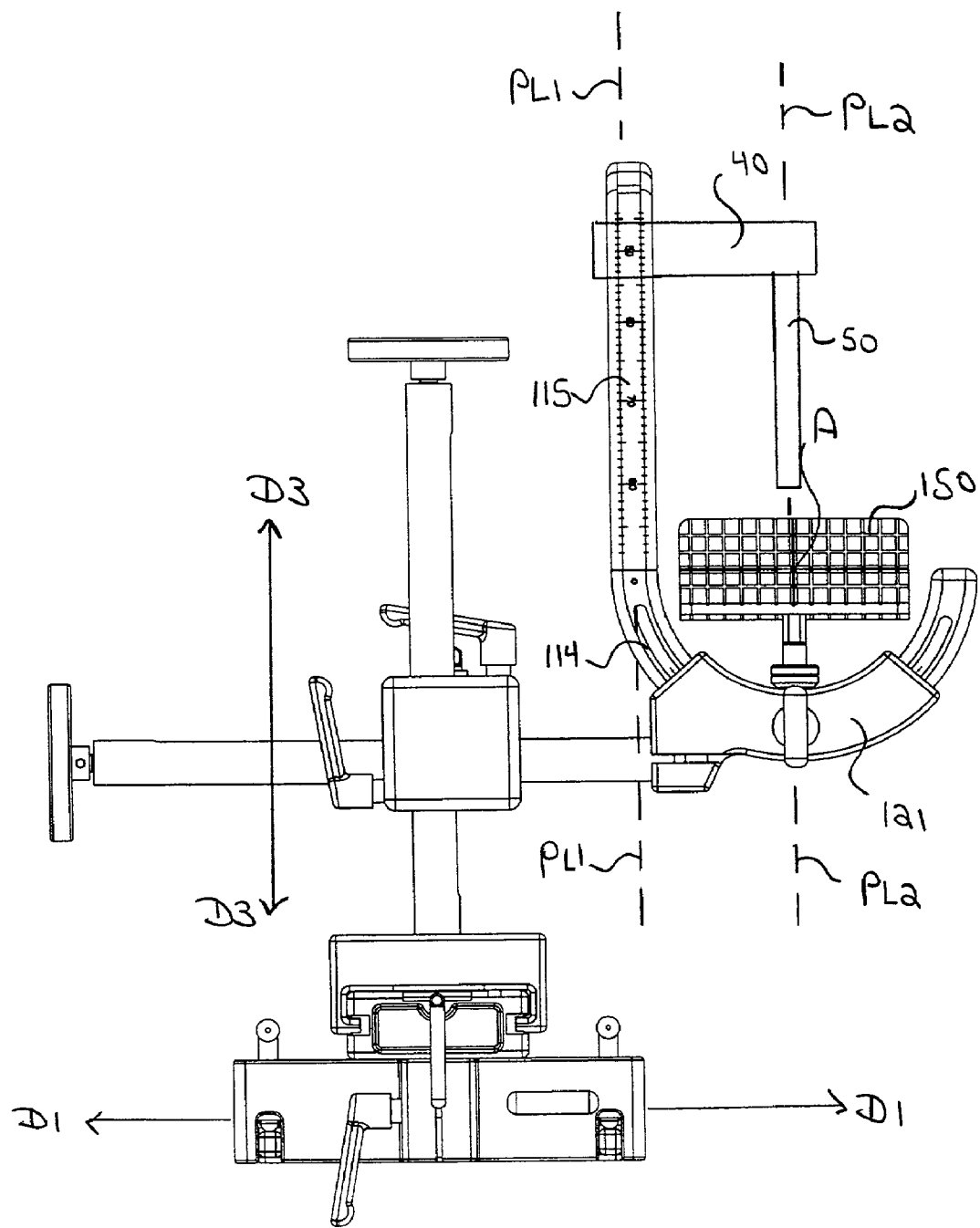
FIG. 14 is a right side view of the surgical guideframe of FIG. 12.
Figure 15:
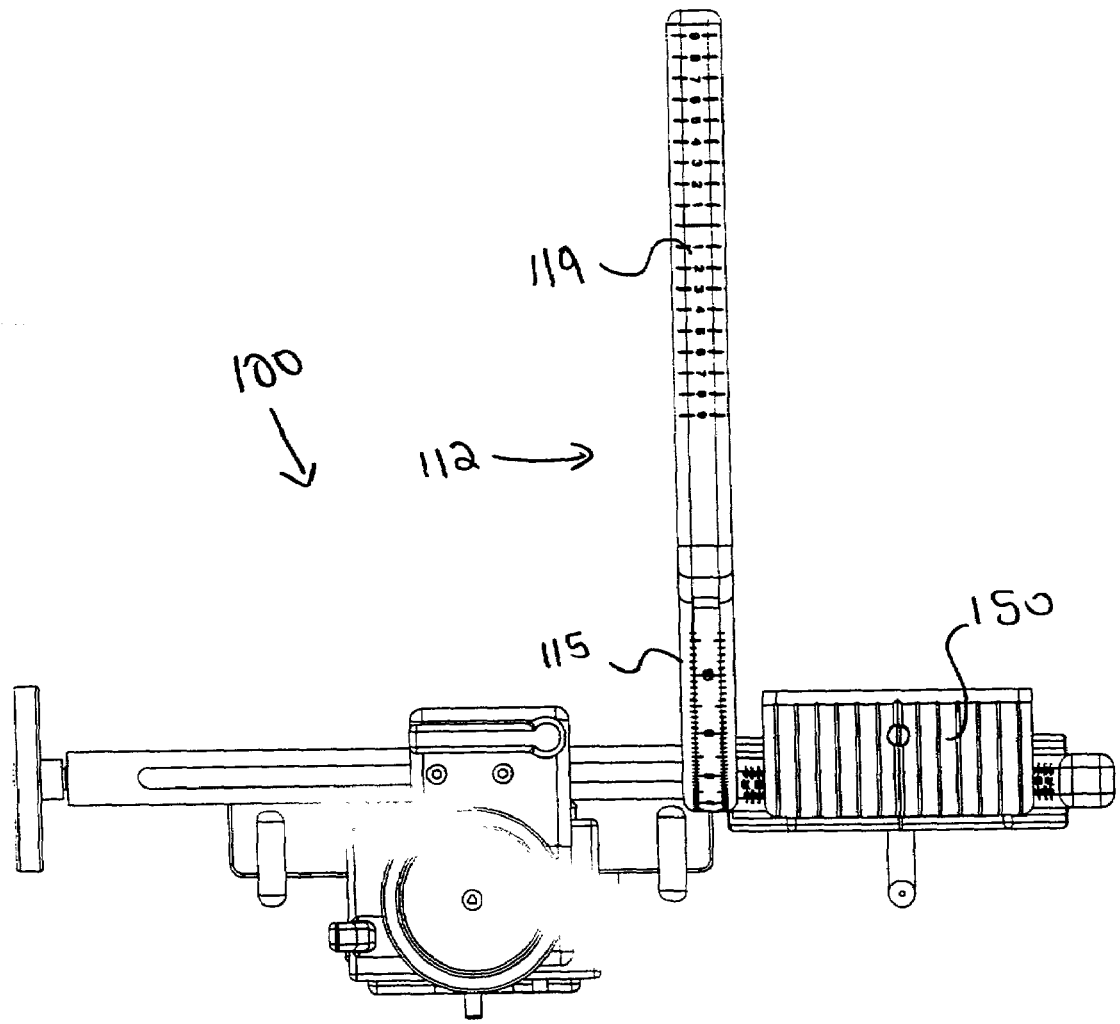
FIG. 15 is a top plan view of the surgical guideframe of FIG. 12.

As shown in FIGS. 14 and 16, a surgical instrument holder 40 (holding a surgical instrument 50) can be adjustably positioned along curved center portion 115 of cross member 112. As can be seen, movement of surgical instrument holder 40 along curved center portion 115 of cross member 112 results in surgical instrument 50 being rotated about point P1 while remaining disposed within plane PL2.

As is also shown in FIG. 14, an alignment target 150 may optionally be attached to curved end portion 114 of cross member 112. Alignment target 150 preferably indicates the position of axis A as well as the position of plane PL2 (i.e.: the plane in which surgical instrument 50 is disposed).

Figure 16A:
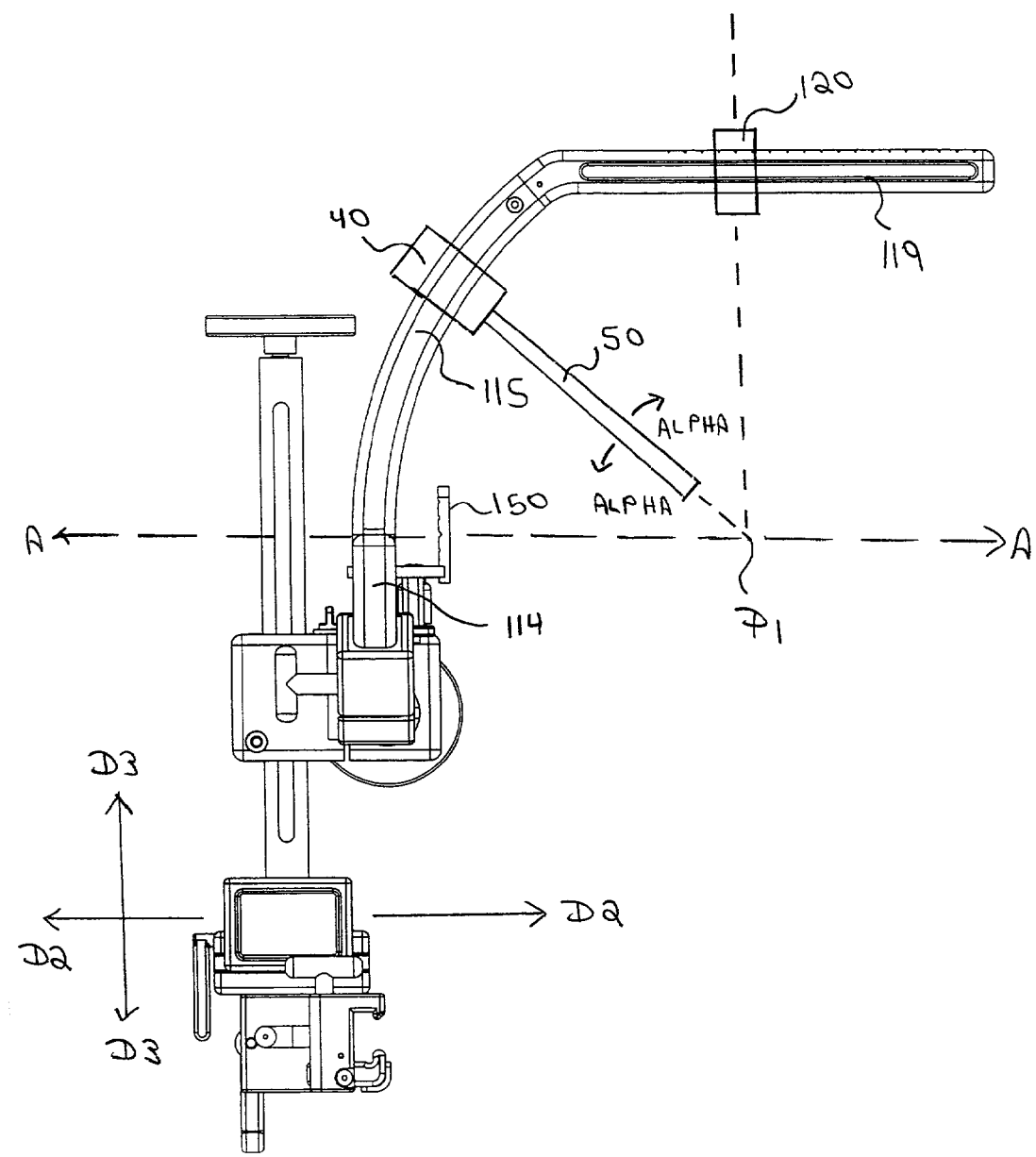
FIG. 16A is a front perspective view of the surgical guideframe of FIG. 12.
Figure 16B:
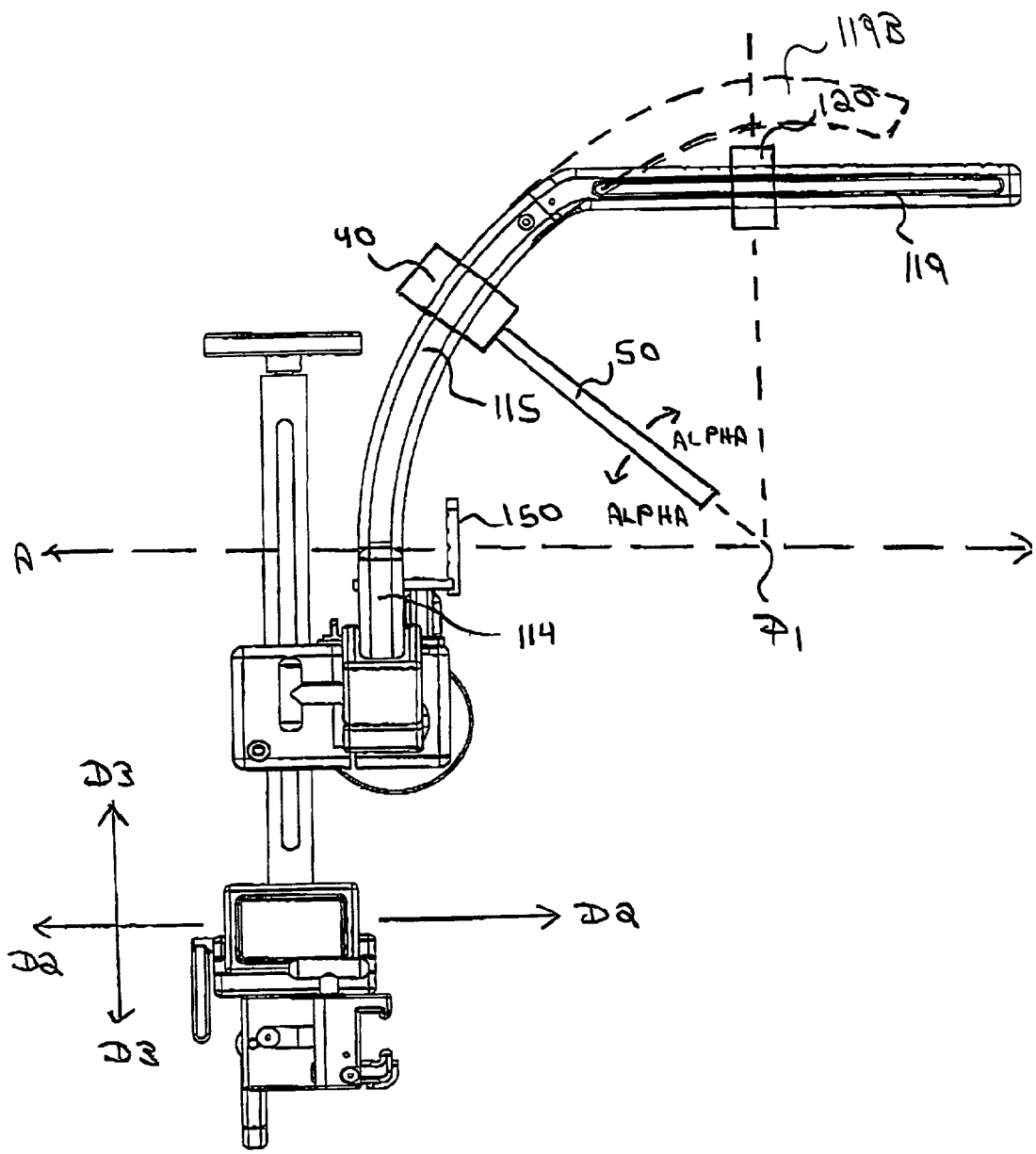
FIG. 16B is a view similar to FIG. 16A, but instead showing an extended curved portion 119B in dotted lines.

Cross member 112 may also comprise a straight portion or free end 119. In preferred aspects, straight portion 119 is disposed parallel to axis A. As shown in FIG. 16B, portion 119B may alternatively not be straight. Rather, portion 119B may be curved, and may have a different radius of curvature from curved center portion 115. Moreover, portion 119B may extend to a distance such that it can be used to position a surgical instrument from an opposite side of the patient from illustrated surgical instrument holder 40. Moreover, portion 119B may extend to a distance such that curves downwardly, resting on the patient or on the operating table, thus providing additional support for instruments suspended by surgical instrument holder(s) 40 positioned on curved portion 115 or portion 119B.

Returning to FIG. 16A, a coronal or mid-sagittal marker 120 may be disposed along straight portion 119. Coronal marker 120 may be positioned directly over a target tissue in a patient (e.g.: a patient's intervertebral space). Such positioning is preferably accomplished by viewing an anterior-posterior image through the patient, thereby positioning marker 120 directly over point P1 in a target tissue. As such, the position of surgical instrument holder 40 along curved portion 115 results in the selection of the preferred angle ALPHA at which surgical instrument 50 is positioned in plane PL2.

Various systems are provided for aligning the present guideframes to position one or more surgical instruments in preferred planes passing through a patient's body. The first system of having a pair of radiopaque markers (16 and 18) positioned along axis A (at opposite curved ends 14 of cross member 12 has been described.

Laser alignment systems are also provided. In each of these various laser or radiopaque marker systems, a first preferred step is to take a radio-image in a preferred path through the patient. This path may be determined by adjusting the position of a C-arm image-intensifier while taking a view through the patient. After the C-arm image-intensifier has been positioned to view along the preferred path, the guideframe is then moved into position such that axis A is aligned with the preferred path. Thereafter, the operator will select a preferred plane at which surgical instruments are to be positioned. (Preferably, the preferred path will pass along the selected plane).

FIG. 17 illustrates a first laser alignment system as follows. A C-arm image intensifier 200 is positioned to take an image in a preferred path PP through a target tissue region T of patient P. It is then determined to be desirable to position surgical instruments in selected plane PLS. Image intensifier 200 is positioned such that preferred path PP passes between the centers of emitter 205 and receiver 206 of image intensifier 200.

A laser source 300 is positioned at each of curved end portions 14. Laser sources 200 each emit a laser beam LB outwardly along axis A. In accordance with the present invention, guideframe 10 is then moved such that laser beam LB is aligned at the centers of emitter 201 and receiver 202 of C-arm image intensifier 200. In other words, guideframe 10 is moved such that laser beam LB is aligned (co-incident) with preferred path PP. This movement is show by arrows M.

A reticle or indicia 201 and 203 marked directly on the emitter and receiver are preferably provided such that laser beams LB can be centered on the emitter and receiver of the C-arm.

FIG. 17B is similar to FIG. 17 but instead shows a single laser source 301 emitting laser beams in both directions along axis A. After a preferred path PP along PLS between emitter 201 and receiver 202 of C-arm image intensifier 200 has been selected by the operator (see FIG. 17A), guideframe 10 is then moved such that laser beam LB is aligned at the centers of emitter 201 and receiver 202 of C-arm image intensifier 200. It is to be understood that a laser source similar to that shown in FIGS. 17A and 17B may also be used to align guideframe 100.

FIG. 17C illustrates another alignment system in which a laser source 301 emits a planar laser beam in two perpendicular planes 303 and 305. Planes 303 and 305 intersect along axis A. In accordance with this aspect of the invention, the emitter 205 and/or receiver 206 of image intensifier 200 preferably has indicia 203 printed thereon indicating the plane (PL2) in which the C-arm is disposed. Stated another way, the C-arm image intensifier is rotated in plane (PL2) when, for example, switching from taking a lateral to an anterior-posterior view through the patient. Indicia 203 remain disposed in plane PL2 during this rotation.

In a preferred method of operation, cross member 112 is positioned in alignment with the C-arm image intensifier by positioning the intersection of planes 303 and 305 at the intersection of indicia 201 and 203.

FIG. 18A illustrates yet another alignment system in which a laser emitter 400 emits a laser beam in perpendicular planes 403 and 405. (Guideframe 10 or 110 is not shown for clarity of illustration). FIG. 18B illustrates further details of this invention. Specifically, laser emitter 400 may comprise a first pair of lasers 402 which both emit a planar laser beam spreading out along plane 403 and a second pair of lasers which both emit a planar laser beam spreading out along plane 405. In preferred aspects, laser emitter 400 is mounted to the C-arm such that the intersection of planes 403 and 405 passes between the centers of the emitter 205 and receiver 206 of the C-arm.

Figure 18C:
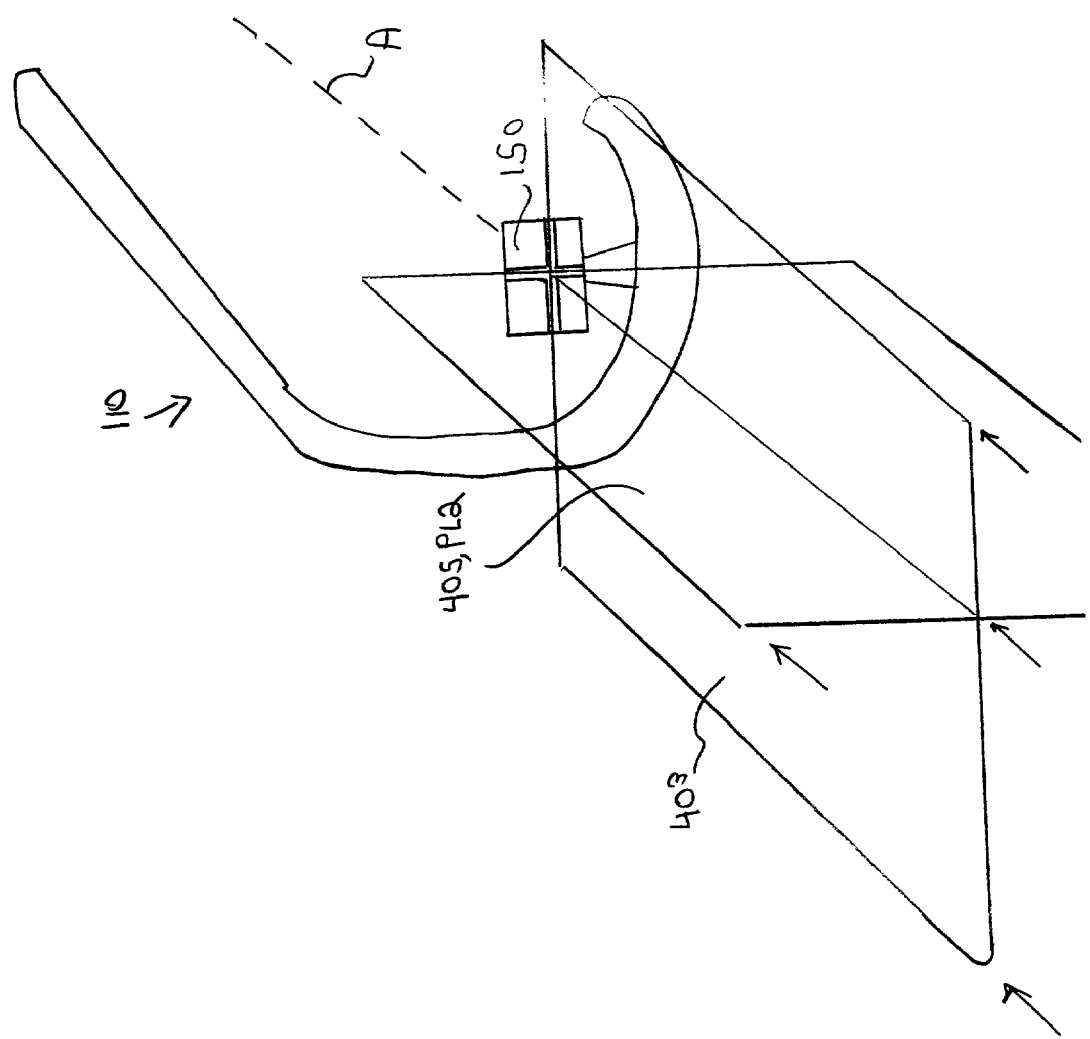
FIG. 18C is an illustration of the laser beam of FIG. 18A being used to align the present quarter-circular cross member guideframe.

In preferred aspects, guideframe 10 (or guideframe 110, or any other guideframe) is then positioned such that its axis A is aligned with the intersection of laser beam planes 403 and 405. For example, as is seen in FIG. 18C, laser beam planes 403 and 405 can be projected onto alignment target 150. Specifically, guideframe 110 can be moved such that its axis A is positioned in alignment with the intersection of planes 403 and 405, and rotated to an angle such that plane PL2 is aligned with plane 405.

An equally important application of laser emitter 400 is that it need not be used with any guideframe at all, as follows. Returning to FIG. 18C, a patient can be positioned between emitter 205 and receiver 206. An image can then be taken in a preferred path through the patient. In the absence of any guideframe, laser beam planes 403 and 405 will project an illuminated cross directly on the patient's skin. The center of this cross will preferably be positioned directly along the preferred path through the patient. Accordingly, laser emitter 400 may be used in any sort of medical procedure to locate a point of surgical entry through the patient's skin. Laser emitter 400 may also be used in open surgical procedures to easily indicate the location of a point along the preferred viewed path through the patient.

An advantage of laser emitter 400 comprising a plurality of laser sources which are off-set from the viewed path (i.e.: the path between the emitter and receiver of the image intensifier) is that no laser source is positioned directly along the preferred viewing path. As such, the laser(s) does not block the viewed image by showing up in the viewed radio-image.

In preferred aspects of the invention, a first pair of laser sources 402 and a second pair of laser sources 404 are used to emit laser beams in planes 403 and 405. It is to be understood that a single laser source 402 and a single laser source 404 may instead be used to emit laser beams in planes 403 and 405. Accordingly, the present invention may comprise only two laser sources, instead of four laser sources.

FIG. 18B illustrates the alignment of guideframe 100. Specifically, guideframe 100 is moved into a position such that target 150 is positioned in alignment with axis A. Specifically, the guideframe is moved such that its axis A (which is centrally located on target 150) is positioned at the intersection of planes 403 and 405. Cross member 112 is then rotated about axis A such that its plane PL2 is disposed in alignment with plane 405.

It is to be understood the alignment system illustrated in FIGS. 17A and 17B could instead be used with guideframe 100 and that the alignment system illustrated in FIGS. 18A and 18B could instead be used with guideframe 10.

Figure 20:
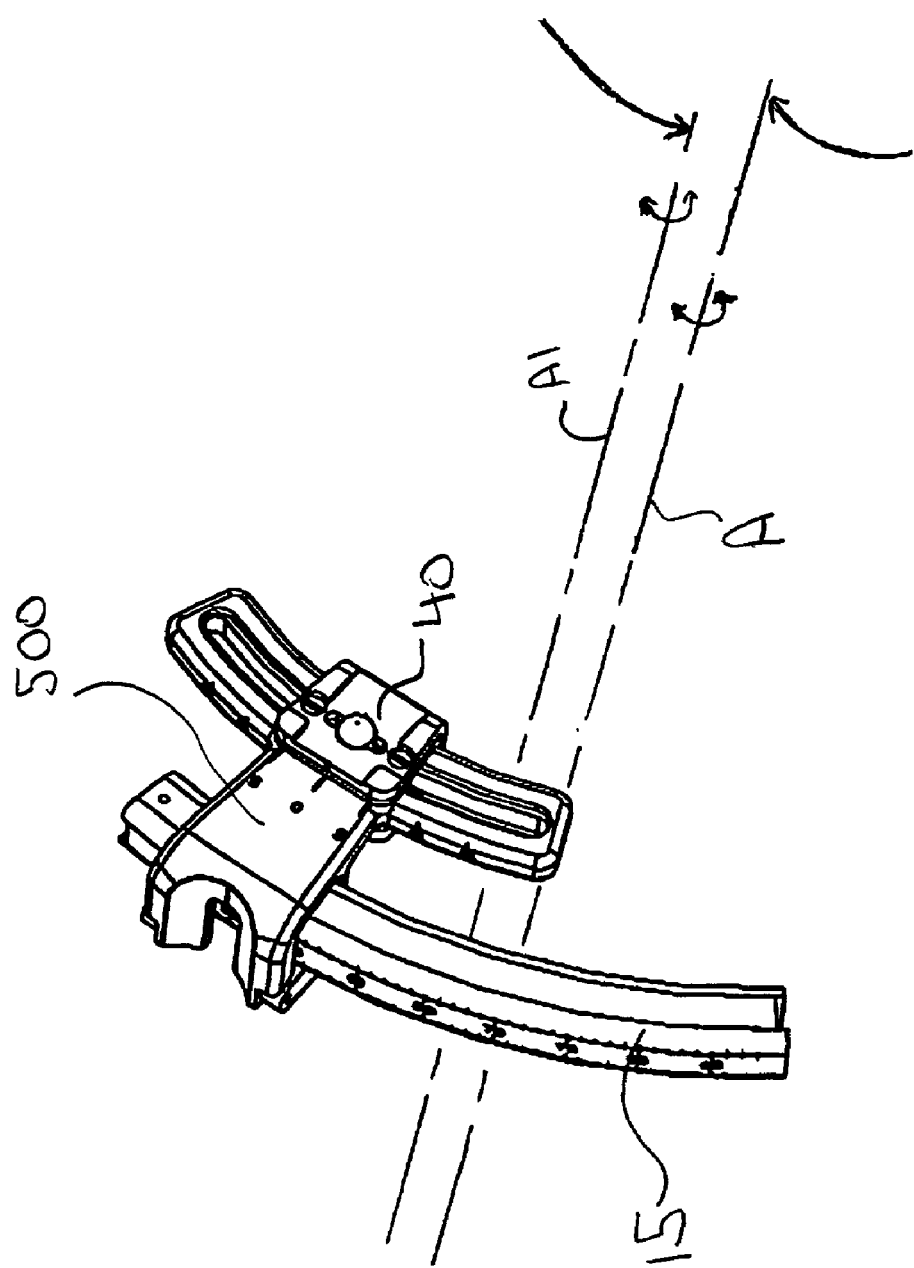
FIG. 20 is a perspective illustration of an intraoperative freedom guide.
Figure 21:
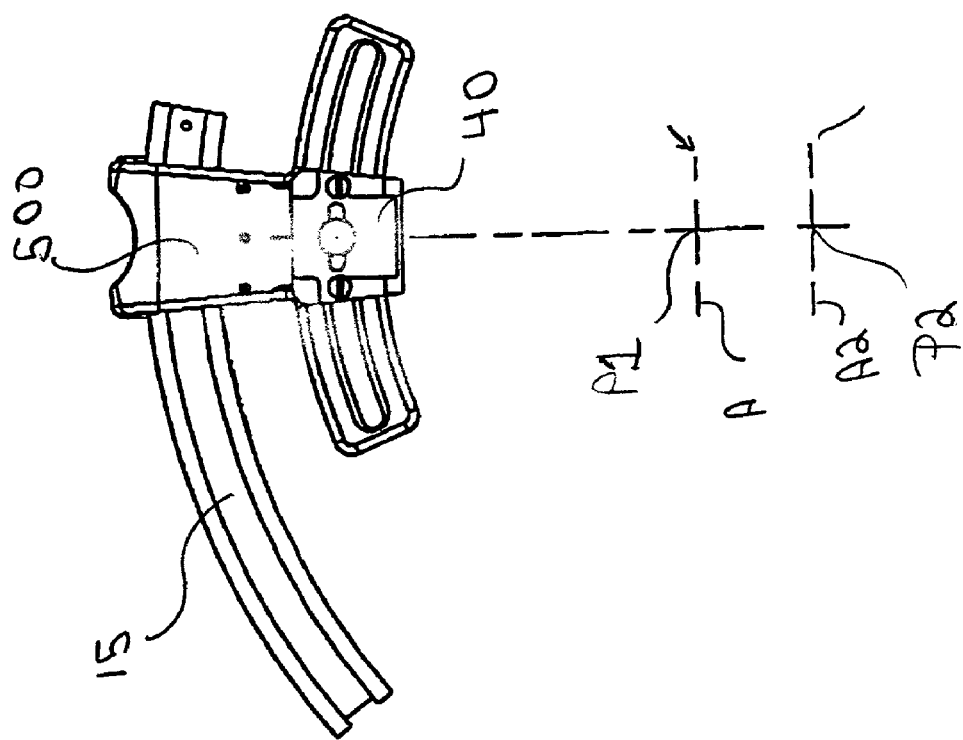
FIG. 21 is a front elevation view of the intraoperative freedom guide of FIG. 20.

FIG. 19 shows a guide 500 which may be attached to guideframe 110 (or guideframe 10) permitting movement of surgical instrument holder 40 back and forth indirection R4 (in plane PL2). Guide 500 permits an additional degree of freedom of movement of a surgical instrument (not shown) held within surgical instrument holder 40. Guide 500 may be positioned on portion 119 of guideframe 110 or on curved center portion 15 of cross member 10 (FIG. 20). As shown in FIG. 21, guide 500 can be used to rotate a surgical instrument (not shown) about point P2 (on axis A2). Should guide 500 not be used, the surgical instrument (not shown) would instead rotate about point P1 (on axis A).

A third embodiment of the present guideframe is shown in FIGS. 22 and 23. Specifically cross member 150 is similar to the first embodiment (i.e. having supports at either end), and is also similar to the second embodiment (i.e.: having a straight portion 119 disposed parallel to axis A.

What is claimed is:

1. A surgical instrument positioning system, comprising:
   a pair of supports;
   a cross member having opposing first and second curved ends and a curved center section extending between the supports, the curved center section disposed within a first plane, the first curved end disposed within a second plane and the second curved end disposed within a third plane; and
   at least one surgical instrument holder suspended from the cross member;
   wherein the second and third planes are each generally perpendicular to the first plane and the first and second curved ends each curve about an axis laterally offset from the first plane.

2. The system of claim 1, wherein the surgical instrument holder is positionable along a length of the curved center section of the cross member.

3. The system of claim 2, wherein movement of the surgical instrument holder along the length of the curved center section of the cross member results in rotation of the surgical instrument holder about a point disposed on an axis passing through centers of curvature of the first and second curved ends.

4. The system of claim 1, wherein the surgical instrument holder positions a surgical instrument in a plane along which an axis extending through centers of curvature of the first and second curved ends passes.

5. A surgical instrument positioning system, comprising:
   at least one support;
   a cross member having a central section disposed in a first plane and at least one curved end portion disposed in a second plane which is generally perpendicular to the first plane, the at least one curved end portion being held by the at least one support such that the cross member is rotatable about an axis which is laterally offset from the first plane and extending through a center of curvature of the at least one curved end portion of the cross member; and at least one surgical instrument holder suspended from the cross member.

6. The system of claim 5, wherein the surgical instrument holder is positionable along a length of the cross member.

7. The system of claim 6, wherein the surgical instrument holder is positionable along a curved section of the cross member.

8. The system of claim 7, wherein movement of the surgical instrument holder along the length of the curved section of the cross member results in rotation of the surgical instrument holder about a point disposed on the axis passing through the center of curvature of the at least one curved end portion of the cross member.

9. The system of claim 5, wherein the surgical instrument holder is dimensioned to position a surgical instrument in a plane along which the axis extending through the center of curvature of the at least one curved end portion of the cross member passes.

10. The system of claim 5, wherein the cross member has only one curved end portion.

11. The system of claim 10, wherein the cross member further comprises a straight portion disposed at an end opposite to the curved end portion.

12. The system of claim 11, wherein the straight portion is parallel to the axis passing through the center of curvature of the curved end portion of the cross member.

13. The system of claim 11, further comprising:
a coronal marker positioned on the straight portion of the cross member.

14. The system of claim 10, wherein the portion of the cross member disposed between the straight portion and the curved end portion is curved in a direction perpendicular to the curved end portion.

15. The system of claim 10, wherein the at least one support comprises a single support holding the one curved end portion of the cross member.

16. The system of claim 5, wherein the cross member has two opposite curved end portions.

17. The system of claim 16, wherein the at least one support comprises a pair of supports, each support holding one of the opposite curved end portions of the cross member.

18. The system of claim 16, further comprising:
a radiopaque height marker attached to one of the curved end portions of the cross member.

19. The system of claim 18, further comprising:
a radiopaque lordotic angle marker attached to the other of the curved end portions of the cross member.

20. The system of claim 19, wherein both the height marker and the lordotic angle marker are positioned on the axis extending through the center of curvature of the opposite curved end portions of the cross member.

21. The system of claim 5, wherein the at least one support comprises a curved sleeve and wherein the at least one curved end portion of the cross member is slidably positionable within the curved sleeve.

22. The system of claim 5, further comprising:
an alignment target attached to one of the at least one curved end portions of the cross member.

23. The system of claim 22, wherein the alignment target indicates the position of the axis extending through the center of curvature of the at least one curved end portion of the cross member.

24. The system of claim 22, wherein the alignment target indicates the position of a plane along which the axis extending through the center of curvature of the at least one curved end portion of the cross member passes.

25. The system of claim 24, wherein the surgical instrument holder positions a surgical instrument in the plane passing through the axis extending through the center of curvature of the at least one curved end portion of the cross member.

26. The system of claim 5, wherein the at least one support adjustably positions the cross member in a vertical direction.

27. The system of claim 5, wherein the at least one support adjustably positions the cross member in a first horizontal direction.

28. The system of claim 27, wherein the at least one support adjustably positions the cross member in a second horizontal direction, the second horizontal direction being perpendicular to the first horizontal direction.

29. The system of claim 5, further comprising:
at least one alignment laser source attached to one of the curved end portions of the cross member.

30. The system of claim 29, wherein the at least one alignment laser source emits a laser beam in a plane passing through the center of curvature of the at least one curved end portion of the cross member.

31. The system of claim 30, wherein the at least one alignment laser source emits a laser beam in two planes passing through the center of curvature of the at least one curved end portion of the cross member.

32. The system of claim 31, wherein the two planes are perpendicular to one another.

33. The system of claim 32, wherein the surgical instrument holder positions a surgical instrument in one of the two planes.

34. The system of claim 33, wherein the surgical instrument holder positions the surgical instrument in the plane along which the axis extending through the center of curvature of the at least one curved end portion of the cross member passes.

35. The system of claim 5, wherein the surgical instrument holder supports an elongated surgical instrument such that the distal end of the surgical instrument is positioned at, proximal to, or pointing towards a point on the axis extending through the center of curvature of the at least one curved end of the cross member.

36. The system of claim 35, wherein the distal end of the surgical instrument remains positioned at, proximal to, or pointing towards the point on the axis passing through the at least one curved end of the cross member as the surgical instrument holder is moved to various positions along the length of the cross member.

37. The system of claim 5, wherein the surgical instrument is an operating cannula.

38. The system of claim 5, wherein the cross member is radio-lucent.

39. A method of positioning a surgical instrument in a selected plane passing through a patient's body, comprising:
positioning a patient under a cross member having a curved central section which spans between two supports on either side of the patient and is disposed in a first plane, the cross member having opposite curved ends which are disposed in second planes which are perpendicular to the first plane, the ends being curved about an axis which is laterally offset from the first plane, and the opposite curved ends each being supported by one of the supports;
adjusting the position of the cross member such that an axis passing through the centers of curvature of the opposite ends of the cross member also passes through a surgical target region on the selected plane;

adjusting the position of the cross member such that a plane disposed parallel to the curved center section of the cross member is disposed in the selected plane; and adjusting the position of a surgical instrument holder suspended from the cross member such that a surgical instrument suspended in the surgical instrument holder is positioned at a preferred angle in the selected plane.

40. A method of positioning a surgical instrument in a selected plane passing through a patient's body, comprising:

positioning the patient under a cross member disposed in a first plane and having a surgical instrument holder suspended therefrom, the cross member having a curved end portion held by a support and is disposed in a second plane generally perpendicular to the first plane, such that the cross member is rotatable about an axis extending through the center of curvature of the curved end portion and laterally offset from the first plane, the surgical instrument holder being positioned to hold a surgical instrument in a plane in which the axis extending through the center of curvature of the curved end portion of the cross member is disposed;

adjusting the position of the cross member such that the axis extending through the center of curvature of the at least one curved end portion of the cross member is disposed in the selected plane; and rotating the cross member about the axis extending through the center of curvature of the at least one curved end portion of the cross member such that the plane in which the surgical instrument is held is aligned with the selected plane.

41. The method of claim 40, wherein adjusting the position of the cross member such that the axis extending through the center of curvature of the at least one curved end portion of the cross member is disposed in the selected plane comprises:

adjusting the vertical height of the cross member.

42. The method of claim 40, wherein adjusting the position of the cross member such that the axis extending through the center of curvature of the at least one curved end portion of the cross member is disposed in the selected plane comprises:

adjusting the cephal-caudal positioning of the cross member.

43. The method of claim 40, wherein adjusting the position of the cross member such that the axis extending through the center of curvature of the at least one curved end portion of the cross member is disposed in the selected plane comprises:

adjusting the lateral positioning of the cross member.

44. The method of claim 40, wherein adjusting the position of the cross member such that the axis extending through the center of curvature of the at least one curved end portion of the cross member is disposed in the selected plane comprises:

rotating the cross member about a vertical axis.

45. The method of claim 40, wherein adjusting the position of the cross member such that the axis extending through the center of curvature of the at least one curved end portion of the cross member is disposed in the selected plane comprises:

rotating the cross member about a horizontal axis.

46. The method of claim 40, wherein adjusting the position of the cross member such that the axis extending through the center of curvature of the at least one curved end portion of the cross member is disposed in the selected plane comprises:

viewing an image of the patient with a C-arm image intensifier in a direction along the selected plane; and aligning the cross member to the C-arm image intensifier.

47. The method of claim 46, wherein aligning the cross member to the C-arm image intensifier comprises:

aligning a pair of radiopaque markers disposed on opposite ends of the cross member with the direction along the selected plane.

48. The method of claim 46, wherein aligning the cross member to the C-arm image intensifier comprises:

emitting a laser beam from a laser source attached to cross member; and aligning the laser beam with a target on the C-arm image intensifier.

49. The method of claim 48, wherein the laser beam is directed along the axis extending through the center of curvature of the at least one curved end portion of the cross member.

50. The method of claim 48, wherein emitting a laser beam from a laser source attached to cross member comprises:

emitting a laser beam in two planes, wherein the planes intersect along the axis extending through the center of curvature of the at least one curved end portion of the cross member, and wherein the surgical instrument holder positions a surgical instrument in one of the two planes.

51. The method of claim 50, wherein rotating the cross member about the axis extending through the center of curvature of the at least one curved end portion of the cross member such that the plane in which the surgical instrument is held is aligned with the selected plane comprises:

aligning the plane in which the surgical instrument holder positions a surgical instrument with the selected plane.

52. The method of claim 46, wherein aligning the cross member to the C-arm image intensifier comprises:

emitting a laser beam from a laser source attached to the C-arm image intensifier; and aligning the laser beam with a target attached to the cross member, wherein the target indicates the axis extending through the center of curvature of the at least one curved end portion of the cross member.

53. The method of claim 52, wherein emitting a laser beam from a laser source attached to the C-arm image intensifier comprises:

emitting a laser beam in two planes which intersect along the axis extending through the center of curvature of the at least one curved end portion of the cross member, wherein the surgical instrument holder positions a surgical instrument in one of the two planes.

54. The method of claim 53, wherein aligning the laser beam with a target attached to the cross member comprises:

aligning the plane in which the surgical instrument holder positions a surgical instrument with the selected plane.

55. The method of claim 40, further comprising:

adjusting the position of the surgical instrument holder along the cross member such that the surgical instrument suspended by the surgical instrument holder is positioned at a preferred angle in the selected plane.

56. The method of claim 40, further comprising:

aligning a coronal marker disposed on the cross member with a target region disposed in the selected plane.

* * * * *